(12) United States Patent
Boger et al.

(10) Patent No.: US 11,253,511 B2
(45) Date of Patent: Feb. 22, 2022

(54) USE OF LOW DOSE EMETINE FOR INHIBITION OF HUMAN CYTOMEGALOVIRUS (HCMV)

(71) Applicants: THE JOHNS HOPKINS UNIVERSITY, Baltimore, MD (US); THE UNITED STATES OF AMERICA, as represented by the Secretary, Department of Health and Human Services, Bethesda, MD (US)

(72) Inventors: Ravit Boger, Baltimore, MD (US); Marc Ferrer, Potomac, MD (US); Juan Marugan, Gaithersburg, MD (US); Andres Dulcey Garcia, Gaithersburg, MD (US); Noel Terrence Southall, Potomac, MD (US); Xin Hu, Frederick, MD (US)

(73) Assignees: The Johns Hopkins University, Baltimore, MD (US); THE UNITED STATES OF AMERICA, as represented by th, Washington, DC (US)

( * ) Notice: Subject to any disclaimer, the term of this patent is extended or adjusted under 35 U.S.C. 154(b) by 0 days.

(21) Appl. No.: 16/068,208

(22) PCT Filed: Jan. 4, 2017

(86) PCT No.: PCT/US2017/012177
§ 371 (c)(1),
(2) Date: Jul. 5, 2018

(87) PCT Pub. No.: WO2017/120225
PCT Pub. Date: Jul. 13, 2017

(65) Prior Publication Data
US 2019/0022083 A1    Jan. 24, 2019

Related U.S. Application Data

(60) Provisional application No. 62/274,609, filed on Jan. 4, 2016.

(51) Int. Cl.
| | | |
|---|---|---|
| *A61K 31/4745* | (2006.01) | |
| *A61K 31/522* | (2006.01) | |
| *A61P 31/22* | (2006.01) | |
| *A61K 38/05* | (2006.01) | |
| *A61P 31/20* | (2006.01) | |
| *A61K 45/06* | (2006.01) | |
| *A61K 9/00* | (2006.01) | |

(52) U.S. Cl.
CPC ........ *A61K 31/4745* (2013.01); *A61K 31/522* (2013.01); *A61K 38/05* (2013.01); *A61K 45/06* (2013.01); *A61P 31/20* (2018.01); *A61P 31/22* (2018.01); *A61K 9/0019* (2013.01); *A61K 9/0053* (2013.01); *A61K 2300/00* (2013.01); *Y02A 50/30* (2018.01)

(58) Field of Classification Search
CPC ... A61K 31/4745; A61K 31/522; A61K 38/05
See application file for complete search history.

(56) References Cited

U.S. PATENT DOCUMENTS

| 2008/0194574 A1 | 8/2008 | Eikhoff et al. |
| 2014/0148377 A1 | 5/2014 | Bakare |

FOREIGN PATENT DOCUMENTS

| RU | 2520766 C2 | 6/2014 | |
| WO | 2000067776 A9 | 5/2000 | |
| WO | WO2009039972 | * 4/2009 | |
| WO | 2009148623 A2 | 12/2009 | |
| WO | WO2015/157223 | * 10/2015 | ......... A61K 31/5415 |

OTHER PUBLICATIONS

Akinboye et al. The Open Natural Products Journal 2011, 4, 8-15.*
Jasenosky et al. Antimicrobial Agents and Chemotherapy 2010, 3007-3010.*
Haupt, et al., Mdm2 promotes the rapid degradation of p53. Nature. May 15, 1997;387(6630):296-9.
Kabbutat, et al., Regulation of p53 stability by Mdm2. Nature. May 15, 1997;387(6630):299-303.
Diaz, et al., Fine-structure map of the human ribosomal protein gene RPS14. Mol Cell Biol. Apr. 1992; 12(4): 1680-1686.
Kern, et al., Oral Treatment of Murine Cytomegalovirus Infections with Ether Lipid Esters of Cidofovir. Antimicrob Agents Chemother. Sep. 2004; 48(9): 3516-3522.
Knight, The chemotherapy of amoebiasis. J Antimicrob Chemother. Sep. 1980;6(5):577-93.
Muhammad, et al., Antiparasitic alkaloids from Psychotria klugii. J Nat Prod. Jul. 2003;66(7):962-7.
Carney, et al., The chemical, spectral, and biological properties of monomethine cyanine dyes containing 1,3-benzoxazine and quinazoline nuclei. J Med Chem. Sep. 1966;9(5):758-62.
Rosenkranz, et al., Alkaloids induce programmed cell death in bloodstream forms of trypanosomes (Trypanosoma b. brucei). Molecules. Oct. 3, 2008;13(10):2462-73.
Deng, et al., Identification of novel antipoxviral agents: mitoxantrone inhibits vaccinia virus replication by blocking virion assembly. J Virol. Dec. 2007;81(24):13392-402.

(Continued)

*Primary Examiner* — Irina Neagu
(74) *Attorney, Agent, or Firm* — Johns Hopkins Technology Ventures

(57) ABSTRACT

The present invention relates to the field of virology. More specifically, the present invention provides methods and compositions useful for prevention and treatment of human cytomegalovirus (CMV). In one embodiment, a pharmaceutical composition comprises (a) emetine or a derivative thereof; (b) a human cytomegalovirus (HCMV) drug; and (c) a pharmaceutically acceptable carrier. In certain embodiments, the pharmaceutical composition further comprises an adjuvant. In a specific embodiment, the HCMV drug is ganciclovir. In such embodiments, emetine is present at about $\frac{1}{10}$ to about $\frac{1}{100}$ the normal dosage for amebiasis.

4 Claims, 25 Drawing Sheets

Specification includes a Sequence Listing.

(56) References Cited

OTHER PUBLICATIONS

Chaves Valadao, et al., Natural Plant Alkaloid (Emetine) Inhibits HIV-1 Replication by Interfering with Reverse Transcriptase Activity. Molecules. Jun. 22, 2015;20(6):11474-89.
He, et al., Recombinant luciferase-expressing human cytomegalovirus (CMV) for evaluation of CMV inhibitors. Virol J. 2011; 8:40.
Summers, et al., Herpes simplex virus type 1 corneal infection results in periocular disease by zosteriform spread. J Virol. Jun. 2001;75(11):5069-75.
Bliss, the Toxicity of Poisons Applied Jointly. Ann Appl Biol. Aug. 1939;26(3):585-615.
Jilek, et al., A quantitative basis for antiretroviral therapy for HIV-1 infection. Nat Med. Feb. 19, 2012;18(3):446-51.
Iversen, et al., A proviral role for CpG in cytomegalovirus infection. J Immunol. May 1, 2009;182(9):5672-81.
Pizzorno, et al., trans-activation and autoregulation of gene expression by the immediate-early region 2 gene products of human cytomegalovirus. J Virol. Apr. 1988; 62(4): 1167-1179.
Tiscornia, et al., A general method for gene knockdown in mice by using lentiviral vectors expressing small interfering RNA. Proc Natl Acad Sci U S A. Feb. 18, 2003;100(4):1844-8.
Vliegen, et al., Improved detection and quantification of mouse cytomegalovirus by real-time PCR. Virus Res. Dec. 2003;98(1):17-25.
Lal, et al., Clean western blot signals from immunoprecipitated samples. Mol Cell Probes. Dec. 2005; 19(6): 385-388.
Fischer, et al., Generation and characterization of a GCV resistant HCMV UL97-mutation and a drug sensitive UL54 mutation. Antiviral Res. Dec. 2013;100(3):575-7.
Boultwood, The role of haploinsufficiency of RPS14 and p53 activation in the molecular pathogenesis of the 5q-syndrome. Pediatr Rep. Jun. 22, 2011; 3(Suppl 2): e10.
Pelletier, D., et al., "Evaluation of a Published in Silico Model and Construction of a Novel Bayesian Model for Predicting Phospholipidosis Inducing Potential" J. Chem. Inf. Model. 2007, 47, 1196-1205.
Awate, et al., Mechanisms of action of adjuvants. Front Immunol. May 13, 2013;4:114.
Wildum, et al., In vitro drug combination studies of Letermovir (AIC246, MK-8228) with approved anti-human cytomegalovirus (HCMV) and anti-HIV compounds in inhibition of HCMV and HIV replication. Antimicrob Agents Chemother. 2015;59(6):3140-8.
Jabs, et al., Mortality associated with resistant cytomegalovirus among patients with cytomegalovirus retinitis and AIDS. Ophthalmology. Jan. 2010;117(1):128-132.e2.
Schreiber, et al., Antiviral treatment of cytomegalovirus infection and resistant strains. Expert Opin Pharmacother. Feb. 2009;10(2):191-209.
Steininger, Novel therapies for cytomegalovirus disease. Recent Pat Antiinfect Drug Discov. Jan. 2007;2(1):53-72.
Avery, et al., Outcomes in Transplant Recipients Treated With Foscarnet for Ganciclovir-Resistant or Refractory Cytomegalovirus Infection. Transplantation. Oct. 2016;100(10):e74-80.
Kimberlin, et al., Effect of ganciclovir therapy on hearing in symptomatic congenital cytomegalovirus disease involving the central nervous system: a randomized, controlled trial. J Pediatr. Jul. 2003;143(1):16-25.
Kimberlin, et al., Valganciclovir for Symptomatic Congenital Cytomegalovirus Disease NEJM. Mar. 2015;372:933-943.
Krosky, et al., The human cytomegalovirus UL97 protein kinase, an antiviral drug target, is required at the stage of nuclear egress. J Virol. Jan. 2003;77(2):905-14.
Williams, et al., In vitro activities of benzimidazole D- and L-ribonucleosides against herpesviruses. Antimicrob Agents Chemother. Jul. 2003;47(7):2186-92.
Lischka, et al., In vitro and in vivo activities of the novel anticytomegalovirus compound AIC246. Antimicrob Agents Chemother. Mar. 2010;54(3):1290-7.
Kaul, et al., First report of successful treatment of multidrug-resistant cytomegalovirus disease with the novel anti-CMV compound AIC246. Am J Transplant. May 2011;11(5):1079-84.
Winston, et al., Maribavir prophylaxis for prevention of cytomegalovirus infection in allogeneic stem cell transplant recipients: a multicenter, randomized, double-blind, placebo-controlled, dose-ranging study. Blood. Jun. 1, 2008;111(11):5403-10.
Chemaly, et al., Letermovir for Cytomegalovirus Prophylaxis in Hematopoietic-Cell Transplantation. NEJM. May 2014;370:1781-1789.
James, et al., Cyclopropavir inhibits the normal function of the human cytomegalovirus UL97 kinase. Antimicrob Agents Chemother. Oct. 2011;55(10):4682-91.
Mercorelli, et al., A 6-aminoquinolone compound, WC5, with potent and selective anti-human cytomegalovirus activity. Antimicrob Agents Chemother. Jan. 2009;53(1):312-5.
Johnson, et al., Human cytomegalovirus up-regulates the phosphatidylinositol 3-kinase (PI3-K) pathway: inhibition of PI3-K activity inhibits viral replication and virus-induced signaling. J Virol. Jul. 2001;75(13):6022-32.
Johnson, et al., Activation of the mitogen-activated protein kinase p38 by human cytomegalovirus infection through two distinct pathways: a novel mechanism for activation of p38. J Virol. Feb. 2000;74(3):1158-67.
Soroceanu, et al., Platelet-derived growth factor-alpha receptor activation is required for human cytomegalovirus infection. Nature. Sep. 18, 2008;455(7211):391-5.
Evers, et al., Inhibition of human cytomegalovirus signaling and replication by the immunosuppressant FK778. Antiviral Res. Jan. 2005;65(1):1-12.
Mukhopadhyay, et al., Efficacy and Mechanism of Action of Low Dose Emetine against Human Cytomegalovirus. PLoS Pathog. Jun. 23, 2016;12(6):e1005717.
Mastrangelo, et al., A phase I study of emetine hydrochloride (NSC 33669) in solid tumors. Cancer. May 1973;31(5):1170-5.
Panettiere, et al., Experience with emetine hydrochloride (NSC 33669) as an antitumor agent. Cancer. Apr. 1971;27(4):835-41.
Regenthal, et al., Drug levels: therapeutic and toxic serum/plasma concentrations of common drugs. J Clin Monit Comput. Dec. 1999;15(7-8):529-44.
Nair, et al., A simple practice guide for dose conversion between animals and human. J Basic Clin Pharm. Mar. 2016;7(2):27-31.
Dack, et al., Cardiac manifestations of toxic action of emetine hydrochloride in amebic dysentery. Arch Intern Med (Chic). Feb. 1947;79(2):228-38.
Ramachandran, et al., Adverse effects of emetine therapy. Ceylon Med J. Sep. 1973;18(3):138-43.
Shrapnel, et al., Oral emetine in the treatment of intestinal amebiasis. Am J Trap Med Hyg. May 1946;26:293-310.
James, Malaria treated with emetine or metronidazole. Lancet. Aug. 31, 1985;2(8453):498.
Palmer, et al., Reversible myopathy secondary to abuse of ipecac in patients with major eating disorders. N Engl J Med. Dec. 5, 1985;313(23):1457-9.
Yang, et al., Mechanism of emetine cardiotoxicity. Pharmacol Ther. 1980; 10(1):15-26.
Griffiths, et al., Betaherpesviruses in transplant recipients. J Antimicrob Chemother. Apr. 2000;45 Suppl T3:29-34.
Kovacs, et al., Cytomegalovirus infection and HIV-1 disease progression in infants born to HIV-1-infected women. Pediatric Pulmonary and Cardiovascular Complications of Vertically Transmitted HIV Infection Study Group. N Engl J Med. Jul. 8, 1999;341(2):77-84.
Demmler, Infectious Diseases Society of America and Centers for Disease Control. Summary of a workshop on surveillance for congenital cytomegalovirus disease Rev Infect Dis Mar.-Apr. 1991;13(2):315-29.
Manicklal, et al., The "silent" global burden of congenital cytomegalovirus. Clin Microbiol Rev. Jan. 2013;26(1):86-102.
Chou, Cytomegalovirus drug resistance and clinical implications. Transpl Infect Dis. 2001;3 Suppl 2:20-4.
Shen, et al., Dose-response curve slope sets class-specific limits on inhibitory potential of anti-HIV drugs. Nat Med. Jul. 2008;14(7):762-6.

(56) References Cited

OTHER PUBLICATIONS

Thoene, et al., Inhibitors of protein synthesis also inhibit lysosomal proteolysis. Studies using cystinotic fibroblasts. J Clin Invest. Feb. 1985;75(2):370-6.

Madjar, et al., Emetine resistance in Chinese hamster ovary cells is associated with an altered ribosomal protein S14 mRNA. Proc Natl Acad Sci U S A. Feb. 1982;79(4):1003-7.

Zhou, et al., Ribosomal protein S14 unties the MDM2-p53 loop upon ribosomal stress. Oncogene. Jan. 17, 2013;32(3):388-96.

Riley, et al., The Many Faces of MDM2 Binding Partners. Genes Cancer. Mar. 2012; 3(3-4): 226-239.

Kulikov, et al., Binding of p53 to the central domain of Mdm2 is regulated by phosphorylation. J Biol Chem. Sep. 29, 2006;281(39):28575-83.

Moll, et al., The MDM2-p53 interaction. Mol Cancer Res. Dec. 2003;1(14):1001-8.

Worrall, et al., Regulation of the E3 ubiquitin ligase activity of MDM2 by an N-terminal pseudo-substrate motif. J Chem Biol. Aug. 2009; 2(3): 113-129.

Zhang, et al., Evidence that the human cytomegalovirus IE2-86 protein binds mdm2 and facilitates mdm2 degradation. J Virol. Apr. 2006;80(8):3833-43.

Lurain, et al., Antiviral drug resistance of human cytomegalovirus. Clin Microbiol Rev. Oct. 2010;23(4):689-712.

Roy, et al., New cell-signaling pathways for controlling cytomegalovirus replication. Am J Transplant. Jun. 2014;14(6):1249-58.

Madjar, et al., Ribosomal protein S14 is altered by two-step emetine resistance mutations in Chinese hamster cells. Mol Cell Biol. Feb. 1983; 3(2): 190-197.

Browne, et al., Altered cellular mRNA levels in human cytomegalovirus-infected fibroblasts: viral block to the accumulation of antiviral mRNAs. J Virol. Dec. 2001;75(24):12319-30.

Hwang, et al., Human cytomegalovirus IE1-72 protein interacts with p53 and inhibits p53-dependent transactivation by a mechanism different from that of IE2-86 protein. J Virol. Dec. 2009;83(23):12388-98.

Deng, L., et al., "Identification of Novel Antipoxviral Agents: Mitoxantrone Inhibits Vaccinia Virus Replication by Blocking Virion Assembly" Journal of Virology, vol. 81, No. 24, Dec. 2007, p. 13392-13402.

Low, J., "Antiviral Activity of Emetine Dihydrochloride Against Dengue Virus Infection" J Antivir Antiretrovir, vol. 1(1): 062-071 (2009).

\* cited by examiner

| VIRUS | MEAN EC$_{50}$ (μM) ± SD | ASSAY |
|---|---|---|
| HCMV | 0.068 ± 0.00 | PLAQUE |
| GCV-R | 0.038 ± 0.00 | LUCIFERASE |
| HSV-1 | 0.056 ± 0.00 | LUCIFERASE |
| HSV-2 | 0.033 ± 0.00 | PLAQUE |

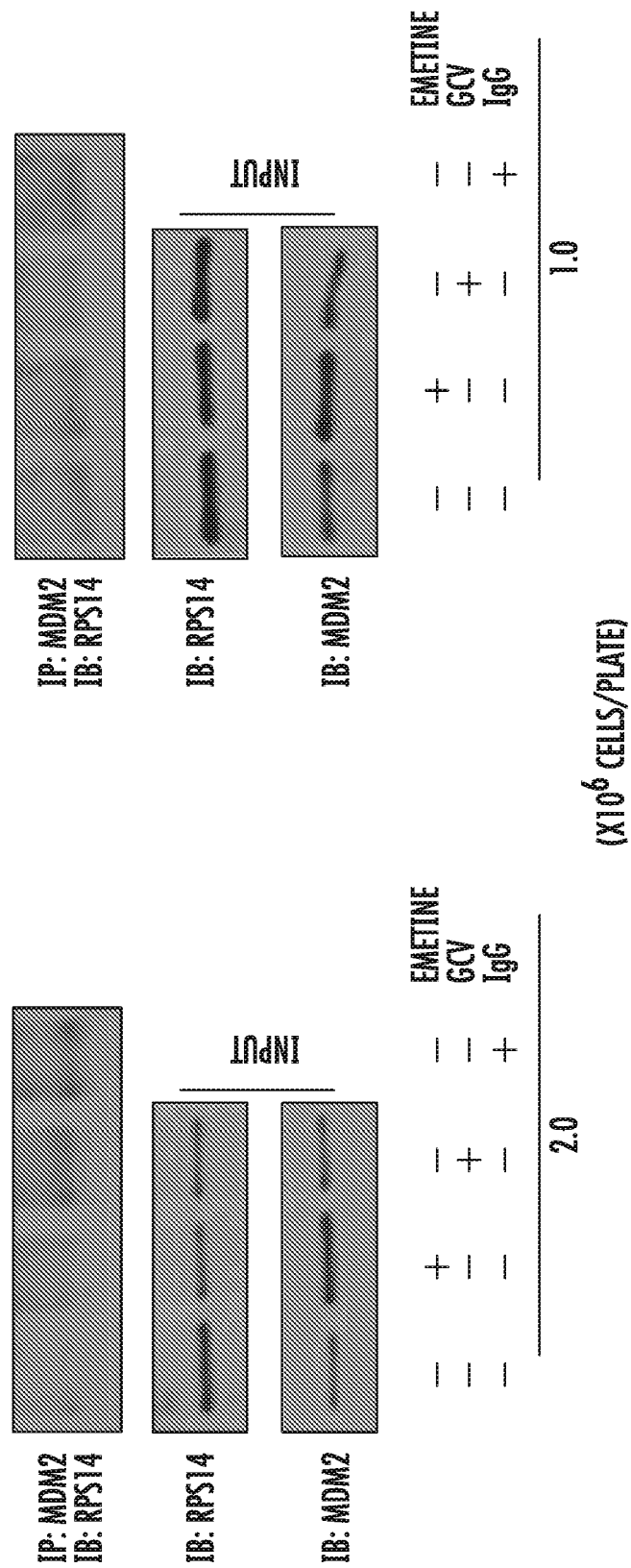

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: gB forward primer

<400> SEQUENCE: 1
agggcttgga gaggacctac a                                           21

<210> SEQ ID NO 2
<211> LENGTH: 19
<212> TYPE: DNA
<213> ORGANISM: Artificial Sequence
<220> FEATURE:
<223> OTHER INFORMATION: gB reverse primer

<400> SEQUENCE: 2
gcccgtcggc agtctagtc                                              19

<210> SEQ ID NO 3
<211> LENGTH: 21
<212> TYPE: DNA
<213> ORGANISM: Artificial Sequence
<220> FEATURE:
<223> OTHER INFORMATION: p21 forward primer

<400> SEQUENCE: 3
tggagactct cagggtcgaa a                                           21

<210> SEQ ID NO 4
<211> LENGTH: 20
<212> TYPE: DNA
<213> ORGANISM: Artificial Sequence
<220> FEATURE:
<223> OTHER INFORMATION: p21 reverse primer

<400> SEQUENCE: 4
cggcgtttgg agtggtagaa                                             20

<210> SEQ ID NO 5
<211> LENGTH: 24
<212> TYPE: DNA
<213> ORGANISM: Artificial Sequence
<220> FEATURE:
<223> OTHER INFORMATION: GAPDH forward primer

<400> SEQUENCE: 5
cggagtcaac ggatttggtc gtat                                        24

```
<210> SEQ ID NO 6
<211> LENGTH: 24
<212> TYPE: DNA
<213> ORGANISM: Artificial Sequence
<220> FEATURE:
<223> OTHER INFORMATION: GAPDH reverse primer

<400> SEQUENCE: 6
agccttctcc atggtggtga agac                                            24
```

USE OF LOW DOSE EMETINE FOR INHIBITION OF HUMAN CYTOMEGALOVIRUS (HCMV)

CROSS-REFERENCE TO RELATED APPLICATIONS

This application is a 35 U.S.C. § 371 U.S. national entry of International Application PCT/US2017/012177, having an international filing date of Jan. 4, 2017, which claims the benefit of U.S. Provisional Application No. 62/274,609, filed Jan. 4, 2016, the content of each of the aforementioned applications is herein incorporated by reference in their entirety.

STATEMENT OF GOVERNMENTAL INTEREST

This invention was made with government support under grant no. DC013550, awarded by the National Institutes of Health. The government has certain rights in the invention.

FIELD OF THE INVENTION

The present invention relates to the field of virology. More specifically, the present invention provides methods and compositions useful for prevention and treatment of human cytomegalovirus (CMV).

INCORPORATION-BY-REFERENCE OF MATERIAL SUBMITTED ELECTRONICALLY

This application contains a sequence listing. It has been submitted electronically via EFS-Web as an ASCII text file entitled "P13919-02_ST25.txt." The sequence listing is 1,419 bytes in size, and was created on Jan. 3, 2017. It is hereby incorporated by reference in its entirety.

BACKGROUND OF THE INVENTION

Infection with Human Cytomegalovirus (HCMV) continues to be a major threat for transplant recipients and patients with AIDS. It is also the most common congenital infection worldwide. Because of the limited drugs approved for HCMV therapy (all viral DNA polymerase inhibitors), the side effects associated with them, and the emergence of resistant viral mutants during therapy, there is a pressing need to develop anti-HCMV compounds with novel mechanisms of action.

SUMMARY OF THE INVENTION

The present invention is based, at least in part, on the discovery that emetine inhibits HCMV replication at very low drug concentrations. The EC50 of emetine is 40 nM and its CC50 is 8 uM, resulting in a selectivity index of 200. HCMV inhibition by emetine required an interaction of ribosomal protein 14 and MDM2. Pharmacokinetic studies performed at NIH-NCATS revealed high tissue concentrations of emetine dosed at 1 mg/kg and a long half-life (24 h). Emetine was well-tolerated in mice. Infection with mouse CMV and emetine treatment revealed high efficacy in mouse CMV inhibition even at 0.1 mg/kg administered orally every 72 h. These in vitro and in vivo studies indicate the potential repurposing of emetine for HCMV, either alone or combined with approved HCMV drugs.

More specifically, as described herein, Emetine inhibits HCMV at an early stage (after entry but before DNA replication), a mechanism that is different from current HCMV inhibitors. In addition, Emetine inhibits mouse CMV replication (in vivo) at a very low dose (0.1 mg/kg) which correlate with human dose of 0.01 mg/kg. HCMV inhibition by emetine involves a novel cellular pathway that requires RPS14 and its binding to MDM2.

Accordingly, in one aspect, the present invention provides compositions for treating or preventing HCMV. In one embodiment, a pharmaceutical composition comprises emetine. In a more specific embodiment, the composition comprises an amount of emetine that is lower than the typical dose of emetine used to treat amebiasis. In certain embodiments, the low dose of emetine is about ½ to about ¹⁄₁₀₀ the normal dose of emetine for amebiasis. In particular embodiments, the low dose of emetine is about ¹⁄₁₀ to about ¹⁄₁₀₀ the normal dose for amebiasis. Thus, in particular embodiments, a pharmaceutical composition comprises a dose of emetine that is about ¹⁄₁₀ to about ¹⁄₁₀₀ of the normal dosage for amebiasis. In further embodiments, the composition further comprises a pharmaceutically acceptable carrier.

In another embodiment, a pharmaceutical composition comprises (a) emetine or a derivative thereof; (b) a vaccine adjuvant; and (c) a pharmaceutically acceptable carrier. The adjuvant can be any adjuvant suitable for treating HCMV including, but not limited to, muramyl dipeptide (MDP), L-Ala-γ-D-Glu-meso-diamino-pimelic acid (tri-DAP) or a derivative of the foregoing. In a further embodiment, the pharmaceutical composition comprises a human cytomegalovirus (HCMV) drug. HCMV drugs include, but are not limited to, ganciclovir, valganciclovir, foscarnet and cidofovir. In certain embodiments, the HCMV drug is ganciclovir. The pharmaceutical composition can be formulated for oral delivery or injection.

The present invention also provides a pharmaceutical composition comprising (a) emetine or a derivative thereof; (b) a human cytomegalovirus (HCMV) drug; and (c) a pharmaceutically acceptable carrier. In certain embodiments, the pharmaceutical composition further comprises an adjuvant. In a specific embodiment, the HCMV drug is ganciclovir. In such embodiments, emetine is present at about ¹⁄₁₀ to about ¹⁄₁₀₀ the normal dosage for amebiasis.

In another aspect, the present invention provides methods for treating HCMV in a patient comprising the step of administering a pharmaceutical composition described herein. The present invention can also be used to treat herpes simplex virus (HSV), Epstein-Barr virus (EBV), Kaposi's Sarcoma-Associated Herpesvirus (KHSV) and the like.

In further embodiments, the pharmaceutical composition is administered orally at a concentration of 0.008 mg/kg. For a 60 kg person, this translates to 0.48 mg or about 0.5 mg per dose. In further embodiments, for people weighing between 40-135 kg, the pharmaceutical composition comprises 0.3-1.1 mg per dose. In more specific embodiments, the composition comprises 0.4-1 mg per dose. In particular embodiments, the pharmaceutical composition is administered 10 doses/month or every 3 days.

In other embodiments, the pharmaceutical composition is administered subcutaneously at a concentration of 0.0094 mg/kg. For a 60 kg person, this translates to 0.564 mg per dose. In further embodiments, for people weighing between 40-135 kg, the pharmaceutical composition comprises 0.3-1.3 mg per dose for subcutaneous administration.

In more specific embodiments, the composition comprises 0.4-1.2 mg per dose. In particular embodiments, the pharmaceutical composition is administered 10 doses/month or every 3 days. In further embodiments, a pharmaceutical composition is provided for oral or subcutaneous injection in a dosage form of 0.5-2 mg.

BRIEF DESCRIPTION OF THE FIGURES

FIGS. 9A-9B: RPS14 does not interact with MDM2 in non-infected emetine treated cells. Cells were seeded at (A) 2 or (B) 1 million/plate in 100 mm dishes, treated with MG132 (10 µM) along with emetine (75 nM) or GCV (5 µM) for 24 h. At 24 hpi, lysates were collected and subjected to immunoprecipitation with anti-MDM2 antibody followed by immunoblotting with anti-RPS14 antibody.

DETAILED DESCRIPTION OF THE INVENTION

Figure 1A:
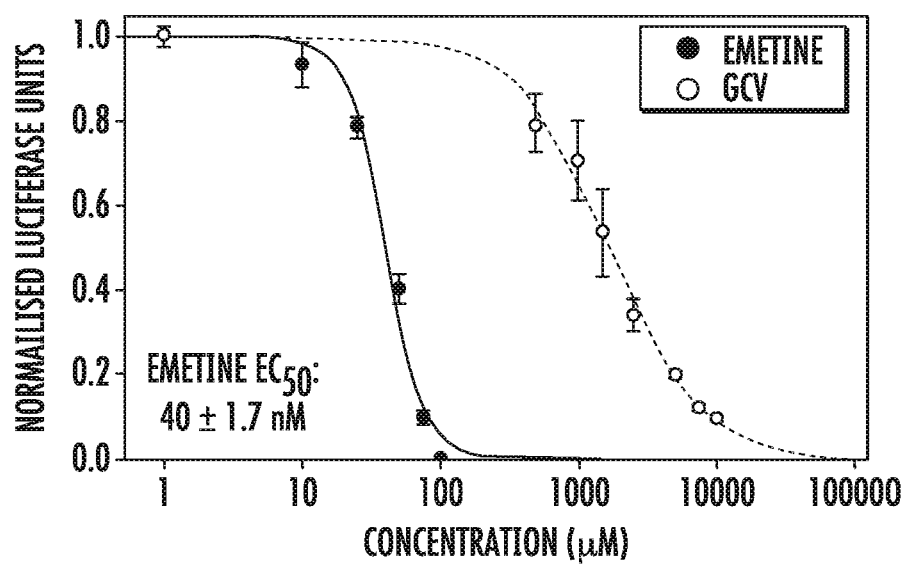
FIGS. 1A-1E: Anti-HCMV activity of emetine and synergy with GCV. A) Emetine fully inhibits HCMV at 75 nM concentration. Cells were infected with pp28-luciferase HCMV Towne and treated with the indicated concentrations of emetine or GCV. Luciferase activity was measured at 72 hpi. Data represent mean±SE of triplicate determinations from a representative of three independent experiments. B) Cells were treated with the indicated concentrations of emetine and cell viability was determined after 72 h. Data represent mean values±SE of triplicate determinations from a representative of three independent experiments. C) $EC_{50}$ value of emetine against different herpesviruses. D) Inhibition of HCMV protein expression by emetine at 72 hpi. Cells were infected with HCMV Towne and treated with emetine. Cell lysates were collected for Western blotting at 72 hpi and expression of viral proteins IE1/2, UL44 and pp65 was determined. E) Cells were infected with pp28-luciferase HCMV Towne, and treated with combination of GCV and emetine. The anti-viral activity was evaluated by luciferase assay. Data represent mean values±the SE of triplicate determinations from a representative of three independent experiments.
Figure 1B:
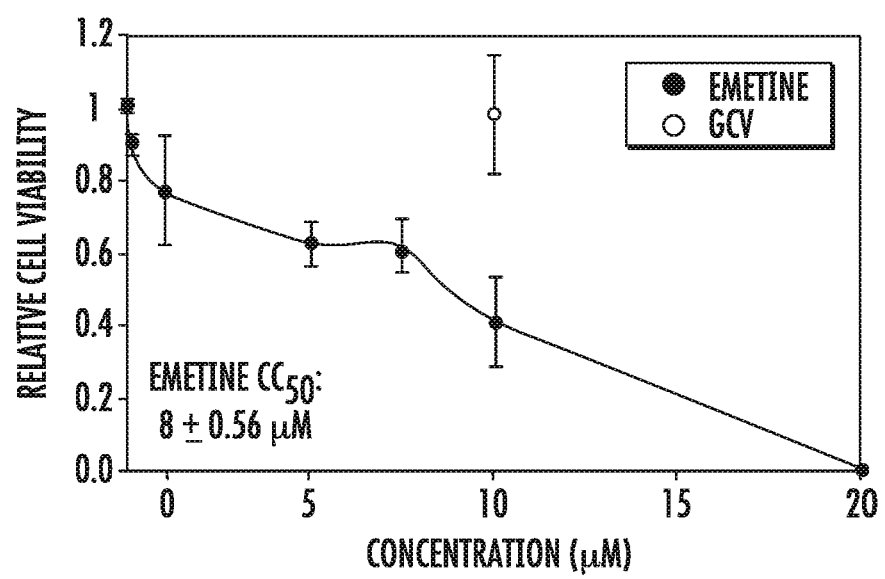

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Infection with human cytomegalovirus (CMV), a member of the herpes virus family, is common in humans. Seroprevalence rates increase with age, reaching 90% in individuals older than 80 years. The virus establishes lifelong persistent infection, which usually remains asymptomatic. In immunocompromised hosts, such as transplant recipients and patients with AIDS, CMV causes significant morbidity and mortality. Over 75% of solid organ transplant recipients are newly infected or reactivate latent CMV after transplantation. Since many organ donors are CMV-positive, recipients often require CMV prophylaxis to prevent CMV disease. CMV-seropositive HIV-infected patients progress 2.5-fold more rapidly to AIDS and death than those who are CMV-seronegative. Despite highly-active antiretroviral therapy, HIV-infected patients remain at risk for CMV disease.

CMV is the most common congenitally-acquired infection causing mental retardation and deafness. It is the leading infectious cause of non-genetic hearing loss and central nervous system (CNS) damage in children. The hearing loss is severe and progressive, significantly impacting the child's life. The estimated annual societal cost of supporting children with congenital CMV approaches $2 billion (1991 US dollars).

The detection of CMV in blood of presumably immunocompetent hosts (viremia) was linked with outcomes of sepsis and pulmonary complications in CMV-seropositive patients treated in intensive care-units. Virus has also been detected in the brain tumor glioblastoma multiforme. Although the direct role of CMV in these syndromes is unclear, virus replication may contribute to their natural history, and the potential benefit of anti-viral therapy in these conditions is currently being investigated in clinical trials. At this time there is no approved CMV vaccine, although several formulations are at different stages of development.

The systemic anti-CMV drugs target the viral DNA polymerase and suppress virus replication. However, their use is associated with considerable toxicities to bone marrow (ganciclovir-GCV) and kidneys (foscamet and cidofovir) and emergence of resistant viruses during prolonged courses of therapy (Jabs, D. A., Martin, B. K. & Forman, M. S. Mortality associated with resistant cytomegalovirus among patients with cytomegalovirus retinitis and AIDS. Ophthalmology 117, 128-132 (2010); Schreiber, A., et al. Antiviral treatment of cytomegalovirus infection and resistant strains. Expert. Opin. Pharmacother 10, 191-209 (2009); Steininger, C. Novel therapies for cytomegalovirus disease. Recent Pat Antiinfect. Drug Discov 2, 53-72 (2007)). A retrospective analysis from Johns Hopkins reveals high rates of complications and mortality in patients treated with foscamet (Avery, R. K., et al. Outcomes in Transplant Recipients Treated with Foscamet for Ganciclovir-Resistant or Refractory Cytomegalovirus Infection. Transplantation (2016)). Until recently, intravenous GCV was the only agent approved for congenital CMV infection with CNS involvement, based on a phase III clinical trial in which hearing preservation or prevention of hearing loss were documented in the treated children (Kimberlin, D. W., et al. Effect of ganciclovir therapy on hearing in symptomatic congenital cytomegalovirus disease involving the central nervous system: a randomized, controlled trial. J. Pediatr 143, 16-25 (2003)). This clinical trial demonstrated that anti-viral therapy has an important role in the outcome of congenital CMV-associated hearing loss. Recent data from a phase III clinical trial of oral valganciclovir (the valyl-ester prodrug of GCV) in congenitally-infected children reveal that 6 months' therapy has better neurological outcome than 6 weeks' therapy, but GCV-resistant mutants emerge (Kimberlin, D. W., et al. Valganciclovir for symptomatic congenital cytomegalovirus disease. N. Engl. J. Med 372, 933-943 (2015)). Widespread use of a limited number of drugs eventually leads to the development of drug resistant strains. New strategies for CMV therapy are needed to treat this chronic disease.

Newly-identified agents that target CMV proteins other than the DNA polymerase are the UL97 kinase inhibitor, maribavir, and the terminase inhibitor, AIC246 (letermovir) (Krosky, P. M., Baek, M. C. & Coen, D. M. The human cytomegalovirus UL97 protein kinase, an antiviral drug target, is required at the stage of nuclear egress. J. Virol 77, 905-914 (2003); Williams, S. L., et al. In vitro activities of benzimidazole D- and L-ribonucleosides against herpesviruses Antimicrob. Agents Chemother 47, 2186-2192 (2003); Lischka, P., et al. In vitro and in vivo activities of the novel anticytomegalovirus compound AIC246 Antimicrob. Agents Chemother 54, 1290-1297 (2010); and Kaul, D. R., et al. First report of successful treatment of multidrug-resistant cytomegalovirus disease with the novel anti-CMV compound AIC246. Am. J. Transplant 11, 1079-1084 (2011)). Maribavir showed efficacy in a phase II clinical trial (Winston, D. J., et al. Maribavir prophylaxis for prevention of cytomegalovirus infection in allogeneic stem cell transplant recipients: a multicenter, randomized, double-blind, placebo-controlled, dose-ranging study. Blood 111, 5403-5410 (2008)), but a phase III trial in bone marrow transplant recipients showed no significant difference in rates of CMV disease between maribavir and placebo recipients. Additional studies are needed to establish the role and indications for use of maribavir. AIC246 completed a phase II clinical trial in 2014 (Lischka, P., et al. In vitro and in vivo activities of the novel anticytomegalovirus compound AIC246 Antimicrob. Agents Chemother 54, 1290-1297 (2010); Kaul, D. R., et al. First report of successful treatment of multidrug-resistant cytomegalovirus disease with the novel anti-CMV compound AIC246. Am. J. Transplant 11, 1079-1084 (2011); and Chemaly, R. F., et al. Letermovir for cytomegalovirus prophylaxis in hematopoietic-cell transplantation. N. Engl. J. Med 370, 1781-1789 (2014)). A few anti-CMV compounds are in pre-clinical stages of evaluation (James, S. H., et al. Cyclopropavir inhibits the normal function of the human cytomegalovirus UL97 kinase Antimicrob. Agents Chemother 55, 4682-4691 (2011); Mercorelli, B., et al. A 6-aminoquinolone compound, WC5, with potent and selective anti-human cytomegalovirus activity. Antimicrob. Agents Chemother 53, 312-315 (2009)).

CMV uses multiple cell signaling pathways to achieve efficient replication. There is an interest in identifying compounds that can modulate cellular pathways critical for CMV replication. Such "host-dependent anti-viral" agents may not be under direct viral control and therefore are less likely to select for resistant mutants. Compounds modulating cellular pathways were reported to inhibit CMV. These can be grouped into inhibitors acting early during virus replication [phosphoinositide 3-kinase (PI3K) inhibitor (Johnson, R. A., Wang, X., Ma, X. L., Huong, S. M. & Huang, E. S. Human cytomegalovirus up-regulates the phosphatidylinositol 3-kinase (PI3-K) pathway: inhibition of PI3-K activity inhibits viral replication and virus-induced signaling. J. Virol 75, 6022-6032 (2001)), $p^{38}$ mitogen-activated protein kinase (MAPKs) (Johnson, R. A., Huong, S. M. & Huang, E. S. Activation of the mitogen-activated protein kinase p38 by human cytomegalovirus infection through two distinct pathways: a novel mechanism for activation of p38. J. Virol 74, 1158-1167 (2000)) and tyrosine kinase inhibitor, Gleevec (Soroceanu, L., Akhavan, A. & Cobbs, C. S. Platelet-derived growth factor-alpha receptor activation is required for human cytomegalovirus infection. Nature 455, 391-395 (2008)), and those active at multiple steps of virus replication—the cyclin-dependent kinase (CDK) inhibitor, roscovitine (Johnson, R. A., Wang, X., Ma, X. L., Huong, S. M. & Huang, E. S. Human cytomegalovirus up-regulates the phosphatidylinositol 3-kinase (PI3-K) pathway: inhibition of PI3-K activity inhibits viral replication and virus-induced signaling. J. Virol 75, 6022-6032 (2001)), leflunomide and its active metabolite FK778 (Evers, D. L., Wang, X., Huong, S. M., Andreoni, K. A. & Huang, E. S. Inhibition of human cytomegalovirus signaling and replication by the immunosuppressant FK778. Antiviral Res 65, 1-12 (2005)). Toxicity associated with these agents precludes their use for CMV therapeutics, especially given the prolonged courses of therapy that are required.

As described herein, the present inventors performed a high throughput screening (HTS) for CMV inhibitors and identified emetine as a CMV inhibitor (Mukhopadhyay, R., et al. Efficacy and Mechanism of Action of Low Dose Emetine against Human Cytomegalovirus. PLoS Pathog 12, e1005717 (2016)). Emetine is an old drug that has been used parenterally for treatment of amebiasis, until it was replaced with metronidazole. In addition, syrup of Ipecac is available over-the-counter and contains significant amount of emetine as one of its active components. Although originally recommended to store in homes with children for induction of vomiting in case of intoxication, the American Academy of Pediatrics no longer endorses its use, and experience has shown that in many cases it did not induce vomiting. There was also variability in emetine concentration between batches of Ipecac. Emetine was also found to have anti-cancer activities for which it has entered clinical trials (Mastrangelo, M. J., Grage, T. B., Bellet, R. E. & Weiss, A. J. A phase I study of emetine hydrochloride (NSC 33669) in solid tumors. Cancer 31, 1170-1175 (1973); Panettiere, F. & Coltman, C. A., Jr. Experience with emetine hydrochloride (NSC 33669) as an antitumor agent. Cancer 27, 835-841 (1971)). Altogether there is clinical experience with emetine at doses up to 600 mg, which should provide exposures considerably above that required for anti-viral activity. As described herein, the in vitro and in vivo data of emetine in CMV inhibition, and its synergistic activity with GCV, support an evaluation at a lower dose in humans.

For amebiasis, emetine has been administered intramuscularly (IM) or subcutaneously (SC) daily at 1 mg/kg (maximal dose of 60 mg) for up to 10 days. Severe side effects occurred rarely and were only observed at high doses. Emetine was well-tolerated when delivered intravenously at 1.5 mg/kg dose twice a week in clinical trials as an anti-tumor agent (Panettiere, F. & Coltman, C. A., Jr. Experience with emetine hydrochloride (NSC 33669) as an antitumor agent. Cancer 27, 835-841 (1971)). Patients treated with 1 mg/kg emetine daily via SC injection for 10 days did not experience any notable toxicity (Mastrangelo, M. J., Grage, T. B., Bellet, R. E. & Weiss, A. J. A phase I study of emetine hydrochloride (NSC 33669) in solid tumors. Cancer 31, 1170-1175 (1973)).

The present inventors found CMV inhibition with emetine at nM concentrations in vitro. The therapeutic plasma concentration of emetine as measured in the past is 0.005-0.075 µg/mL, and its half-life>24-48 h (Regenthal, R., Krueger, M., Koeppel, C. & Preiss, R. Drug levels: therapeutic and toxic serum/plasma concentrations of common drugs. J. Clin. Monit. Comput 15, 529-544 (1999)). As described herein, the in vitro data suggest that at therapeutic plasma concentration CMV replication may be fully inhibited. In addition, PK studies support wide and prolonged tissue distribution, which may be a critical factor in CMV inhibition. In a specific embodiment, the present inventors found that a dose of 0.1 mg/kg administered orally every three days inhibits mouse CMV replication in vivo. Using allometric scaling this could translate into a human dose of 0.008 mg/kg (Nair, A. B. & Jacob, S. A simple practice guide for dose conversion between animals and human. J Basic Clin Pharm 7, 27-31 (2016)). For a 60 kg individual 0.5 mg/dose would be considered for human CMV therapy. In one month, 10 doses (a dose every 3 days) will result in a cumulative dose of 5 mg. Therefore, to reach the 600 mg amebiasis dose 120 months of CMV therapy would need to be provided. The expected cumulative dose with regimens used in general for CMV therapy would be substantially lower than the doses that have been used in the past, even if dosed daily.

I. Definitions

"Agent" refers to all materials that may be used as or in pharmaceutical compositions, or that may be compounds such as small synthetic or naturally derived organic compounds, nucleic acids, polypeptides, antibodies, fragments, isoforms, variants, or other materials that may be used independently for such purposes, all in accordance with the present invention.

A "patient," "subject," or "host," to be treated by the present methods refers to either a human or non-human animal, such as primates, mammals, and vertebrates.

A "small molecule" refers to a composition that has a molecular weight of less than 3 about kilodaltons (kDa), less than about 1.5 kilodaltons, or less than about 1 kilodalton. Small molecules may be nucleic acids, peptides, polypeptides, peptidomimetics, carbohydrates, lipids or other organic (carbon-containing) or inorganic molecules. A "small organic molecule" is an organic compound (or organic compound complexed with an inorganic compound (e.g., metal)) that has a molecular weight of less than about 3 kilodaltons, less than about 1.5 kilodaltons, or less than about 1 kDa.

As used herein, the terms "treatment," "treating," "treat" and the like, refer to obtaining a desired pharmacologic and/or physiological effect. The terms are also used in the context of the administration of a "therapeutically effective amount" of an agent, e.g., emetine. The effect may be prophylactic in terms of completely or partially preventing a particular outcome, disease or symptom thereof and/or may be therapeutic in terms of a partial or complete cure for a disease and/or adverse effect attributable to the disease. "Treatment," as used herein, covers any treatment of a disease in a subject, particularly in a human, and includes:

(a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In particular embodiments, the term is used in the context of preventing or treating HCMV.

II. Pharmaceutical Compositions and Administration

Accordingly, a pharmaceutical composition of the present invention comprises an effective amount of emetine or a derivative thereof. Emetine derivatives include, but are not limited to, dehydroemetine and cephaeline. See also U.S. Patent Publication No. 20140148377. Other derivatives useful as embodiments of the present invention include N-methylemetine, isoemetine, demethoxyemetine, noremetine, psychotrine and methylpsychotrine. The pharmaceutical compositions may further comprise an adjuvant including, but not limited to, muramyl dipeptide (MDP), L-Ala-γ-D-Glu-meso-diamino-pimelic acid (tri-DAP) and derivatives thereof (see U.S. Provisional Patent Application No. 62/194, 908) and/or HCMV drug(s) including, but not limited to, ganciclovir, valganciclovir, foscarnet and cidofovir. In particular embodiments, the adjuvant is MDP or tri-DAP. In certain embodiments, the HCMV drug used in combination with emetine is ganciclovir.

As used herein, the term "effective," means adequate to accomplish a desired, expected, or intended result. More particularly, an "effective amount" or a "therapeutically effective amount" is used interchangeably and refers to an amount of emetine, perhaps in further combination with an adjuvant and/or an HCMV drug, necessary to provide the desired "treatment" (defined herein) or therapeutic effect, e.g., an amount that is effective to prevent, alleviate, treat or ameliorate symptoms of a disease or prolong the survival of the subject being treated. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The pharmaceutical compositions of the present invention are in biologically compatible form suitable for administration in vivo for subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which emetine (and optionally in combination with an adjuvant and/or a second HCMV drug) are administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of emetine (and optionally in combination with an adjuvant and/or a second HCMV) together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In certain embodiments, subcutaneous injection is preferred.

In general, the pharmaceutical compositions comprising emetine may be used alone (e.g., a formulation comprising emetine) or in concert with other therapeutic agents (e.g., an adjuvant and/or HCMV drug) (e.g., emetine composition separate from the other agents or a combination pharmaceutical composition) at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen (e.g., pharmaceutical compositions within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical compositions and various therapeutic agents may be independently optimized and combined to achieve a synergistic result wherein the pathology is reduced more than it would be if either was used alone.

In particular, toxicity and therapeutic efficacy of a pharmaceutical composition disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

In certain embodiments, emetine is administered in low dose amount. The phrase "low dose" or "low dose amount" of emetine in the context of the present invention (alone or in combination with an adjuvant and/or HCMV drug) refers to the use of a particular amount of emetine that is lower than typically used for amebiasis. In certain embodiments a low dose of emetine is less than about $\frac{1}{2}$, $\frac{1}{3}$, $\frac{1}{4}$, $\frac{1}{5}$, $\frac{1}{6}$, $\frac{1}{7}$, $\frac{1}{8}$, $\frac{1}{9}$, $\frac{1}{10}$, $\frac{1}{11}$, $\frac{1}{12}$, $\frac{1}{13}$, $\frac{1}{14}$, $\frac{1}{15}$, $\frac{1}{16}$, $\frac{1}{17}$, $\frac{1}{18}$, $\frac{1}{19}$, $\frac{1}{20}$, $\frac{1}{21}$, $\frac{1}{22}$, $\frac{1}{23}$, $\frac{1}{24}$, $\frac{1}{25}$, $\frac{1}{26}$, $\frac{1}{27}$, $\frac{1}{28}$, $\frac{1}{29}$, $\frac{1}{30}$, $\frac{1}{31}$, $\frac{1}{32}$, $\frac{1}{33}$, $\frac{1}{34}$, $\frac{1}{35}$, $\frac{1}{36}$, $\frac{1}{37}$, $\frac{1}{38}$, $\frac{1}{39}$, $\frac{1}{40}$, $\frac{1}{41}$, $\frac{1}{42}$, $\frac{1}{43}$, $\frac{1}{44}$, $\frac{1}{45}$, $\frac{1}{46}$, $\frac{1}{47}$, $\frac{1}{48}$, $\frac{1}{49}$, $\frac{1}{50}$, $\frac{1}{51}$, $\frac{1}{52}$, $\frac{1}{53}$, $\frac{1}{54}$, $\frac{1}{55}$, $\frac{1}{56}$, $\frac{1}{57}$, $\frac{1}{58}$, $\frac{1}{59}$, $\frac{1}{60}$, $\frac{1}{61}$, $\frac{1}{62}$, $\frac{1}{63}$, $\frac{1}{64}$, $\frac{1}{65}$, $\frac{1}{66}$, $\frac{1}{67}$, $\frac{1}{68}$, $\frac{1}{69}$, $\frac{1}{70}$, $\frac{1}{71}$, $\frac{1}{72}$, $\frac{1}{73}$, $\frac{1}{74}$, $\frac{1}{75}$, $\frac{1}{76}$, $\frac{1}{77}$, $\frac{1}{78}$, $\frac{1}{79}$, $\frac{1}{80}$, $\frac{1}{81}$, $\frac{1}{82}$, $\frac{1}{83}$, $\frac{1}{84}$, $\frac{1}{85}$, $\frac{1}{86}$, $\frac{1}{87}$, $\frac{1}{88}$, $\frac{1}{89}$, $\frac{1}{90}$, $\frac{1}{91}$, $\frac{1}{92}$, $\frac{1}{93}$, $\frac{1}{94}$, $\frac{1}{95}$, $\frac{1}{96}$, $\frac{1}{97}$, $\frac{1}{98}$, $\frac{1}{99}$, $\frac{1}{100}$, $\frac{1}{101}$, $\frac{1}{102}$, $\frac{1}{103}$, $\frac{1}{104}$, $\frac{1}{105}$, $\frac{1}{106}$, $\frac{1}{107}$, $\frac{1}{108}$, $\frac{1}{109}$, $\frac{1}{110}$, $\frac{1}{111}$, $\frac{1}{112}$, $\frac{1}{113}$, $\frac{1}{114}$, $\frac{1}{115}$, $\frac{1}{116}$, $\frac{1}{117}$, 1/118, 1/119, 1/120, 1/121, 1/122, 1/123, 1/124, 1/125, 1/126, 1/127, 1/128, 1/129, 1/130, 1/131, 1/132, 1/133, 1/134, 1/135, 1/136, 1/137, 1/138, 1/139, 1/140, 1/141, 1/142, 1/143, 1/144, 1/145, 1/146, 1/147, 1/148, 1/149, or less than about 1/150 of a normal dose used for amebiasis. In certain embodiments, the low dose of emetine is about 1/100 or less than about 1/10 of the amount used for amebiasis.

In other embodiments, the low dose of emetine is about or less than 1/2 to less than 1/100 of the amount used for amebiasis. In further embodiments, the low dose of emetine is about or less than about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006 or 0.005 times than the typical amount used for amebiasis.

In specific embodiments, a low dose of emetine is about 0.005 mg/kg to about 0.5 mg/kg, more specifically, about 0.006 mg/kg to 0.5 mg/kg, about 0.007 mg/kg to about 0.45 mg/kg, about 0.008 mg/kg to about 0.4 mg/kg, about 0.008 mg/kg to about 0.35 mg/kg, about 0.007 mg/kg to about 0.45 mg/kg, about 0.007 mg/kg to about 0.4 mg/kg, about 0.008 mg/kg to about 0.3 mg/kg, about 0.008 mg/kg to about 0.3 mg/kg, about 0.1 mg/kg to about 0.25 mg/kg, and so on. In a specific embodiment, the low dose of emetine is about 0.008 mg/kg to 0.3 mg/kg. In other embodiments, the low dose of emetine is 0.006 mg/kg to 0.3 mg/kg.

A normal dose of emetine for amebiasis is 0.857 or about 1 mg/kg/day (IM/SC). In certain embodiments, a low dose of emetine is about one tenth to one hundredth the normal dose, e.g., 0.0857 or about 0.1 mg/kg/day to 0.00857 or about 0.01 mg/kg/day.

In other embodiments, a low dose of emetine comprises any amount below about 0.1 mg/kg for oral administration. The low dose can comprise any amount below about 0.095, 0.09, 0.085, 0.08, 0.075, 0.07, 0.065, 0.06, 0.055, 0.05, 0.045, 0.04, 0.035, 0.03, 0.029, 0.028, 0.027, 0.026, 0.025, 0.024, 0.023, 0.022, 0.021, 0.020, 0.019, 0.018, 0.017, 0.016, 0.05, 0.014, 0.013, 0.012, 0.011, 0.010, 0.009, 0.008, 0.007, 0.006, 0.005, 0.004, 0.003, 0.002, or 0.001 mg/kg.

In further embodiments, a low dose of emetine results in a blood concentration range of about 0.005 µg/ml to about 0.075 µg/ml. The concentration can be less than about 0.075 µg/ml, 0.07 µg/ml, 0.06 µg/ml, 0.05 µg/ml, 0.04 µg/ml, 0.03 µg/ml, 0.02 µg/ml, 0.01 µg/ml, 0.009 µg/ml, 0.008 µg/ml, 0.007 µg/ml, 0.006 µg/ml, 0.005 µg/ml. In a more specific embodiment, the blood emetine concentrations are less than about 0.008 µg/ml. In certain embodiments, the blood emetine concentrations are about 0.05-0.075 µg/ml. The concentration can range from about 0.04, 0.05, or 0.06 µg/ml to about 0.07 or 0.08 µg/ml.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

In other embodiments, the pharmaceutical compositions may be administered every other day for about 2 days, every other day for about 3 days, every other day for about 4 days, every other day for about 5 days, every other day for about 6 days, every other day for about 7 days, every other day for about 8 days, every other day for about 9 days, every other day for about 10 days, every other day for about 11 days, every other day for about 12 days, every other day for about 13 days, every other day for about 14 days, every other day for about 15 days, every other day for about 16 days, every other day for about 17 days, every other day for about 18 days, every other day for about 19 days, every other day for about 20 days, every other day for about 21 days, every other day for about 22 days, every other day for about 23 days, every other day for about 24 days, every other day for about 25 days, every other day for about 26 days, every other day for about 27 days, every other day for about 28 days, every other day for about 29 days, every other day for about 30 days, or every other day for about 31 days or more.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days. In certain embodiments, the pharmaceutical composition is administered every other day. In other embodiments, the composition is administered every 3 days.

In further embodiments, the pharmaceutical composition is administered orally at a concentration of 0.008 mg/kg. For a 60 kg person, this translates to 0.48 mg or about 0.5 mg per dose. In further embodiments, for people weighing between 40-135 kg, the pharmaceutical composition comprises 0.3-1.1 mg per dose. In more specific embodiments, the composition comprises 0.4-1 mg per dose. In particular embodiments, the pharmaceutical composition is administered 10 doses/month or every 3 days.

In other embodiments, the pharmaceutical composition is administered subcutaneously at a concentration of 0.0094 mg/kg. For a 60 kg person, this translates to 0.564 mg per dose. In further embodiments, for people weighing between 40-135 kg, the pharmaceutical composition comprises 0.3-1.3 mg per dose for subcutaneous administration. In more specific embodiments, the composition comprises 0.4-1.2 mg per dose. In particular embodiments, the pharmaceutical composition is administered 10 doses/month or every 3 days.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Efficacy and Mechanism of Action of Low Dose Emetine Against Human Cytomegalovirus Infection with human cytomegalovirus (HCMV) is a threat for pregnant women and immunocompromised hosts. Although limited drugs are available for HCMV, development of new agents is desired. Through screening of the LOPAC library, we identified emetine as HCMV inhibitor. Additional studies confirmed the anti-HCMV activities of emetine in human foreskin fibroblasts (HFFs), with $EC_{50}$-40±1.72 nM, $CC_{50}$-8±0.56 µM, and selectivity index of 200. HCMV inhibition occurred after virus entry, but before virus DNA replication and resulted in decreased expression of viral proteins. Synergistic virus inhibition was achieved when emetine was combined with ganciclovir. In a mouse CMV (MCMV) model emetine was well-tolerated, displayed long half-life, preferential distribution to tissues over plasma, and effectively suppressed MCMV. Since HCMV inhibition by emetine decreased significantly in cycling cells in vitro, control of virus inhibition through cell cycle regulators was suspected. Virus sensitivity to emetine dependend on ribosomal protein 14 (RPS14) binding to MDM2, leading to disruption of MDM2-p53 interaction and RPS14 degradation. Interaction of MDM2-p53 was necessary for HCMV replication. In contact-inhibited cells, HCMV induced RPS14 expression, emetine triggered nuclear translocation and binding of RPS14 to MDM2, competing with binding of p53 to MDM2. However, in cycling cells, RPS14 could not disrupt the exisiting MDM2-p53 interaction, resulting in virus escape and loss of emetine effect. Knockdown of RPS14 resulted in loss of HCMV inhibition by emetine, confirming its requirement for emetine activities. Summarized, emetine represents a promising candidate for HCMV therapy/prophylaxis alone or in combination with ganciclovir through a novel host-dependent mechanism.

Materials and Methods

Compounds.
Ganciclovir (GCV), MG132, CPG 2006, and emetine dihydrochloride hydrate were purchased from Sigma-Aldrich (St. Louis, Mo.). Stocks of 10 mM were prepared in DMSO and stored at −80° C.

Viruses.
The pp28-luciferase HCMV Towne strain was constructed as previously described. A GCV-resistant pp28-luciferase HCMV strain, with a C607Y mutation in UL97 was also used. The recombinant viruses express luciferase under the control of the late CMV gene promoter, pp28. Luciferase expression is strongly activated 48-72 hours post infection (hpi). The recombinant viruses provide a highly-sensitive and reproducible reporter system which correlates with the classic plaque reduction assay. The Towne HCMV strain (ATCC VR-977) was used for plaque reduction, quantitative reverse transcriptase PCR, and immunoprecipitation assays. Human herpes virus strains were: luciferase HSV1-KOS/Dlux/oriS and clinical isolates of HSV2. The clinical isolates were provided by the clinical microbiology laboratory with no identifiers that can link to a specific subject. The Johns Hopkins Office of Human Subject Research Institutional Review Board determined that this research qualified for an exemption. Murid Herpesvirus (MCMV: ATCC VR-1399) was used for infection in mice.

Cell Culture, Virus Infection and Anti-Viral Assays.
Human Foreskin Fibroblasts (HFFs) passage 12-16 (ATCC, CRL-2088™) and mouse embryonic fibroblasts (MEFs) passage 9-14 (ATCC, CRL-1658™) were grown in Dulbecco's Modified Eagle Medium (DMEM) containing 10% fetal bovine serum (FBS) (Gibco, Carlsbad, Calif.) in a 5% $CO_2$ incubator at 37° C. Infection with HCMV or HSV was performed in HFFs, and infection with mouse CMV was performed in MEFs. For HCMV, cells were seeded in either a 96-well plate or 100 mm culture plates (Corning Costar, Sigma Aldrich) at 0.5 or 2 million cells/plate. Following 90 minute adsorption, media was removed and cells were washed with PBS. Media containing 4% FBS and compounds were added to each well. Infected treated HFFs were collected at 72 hpi and lysates were assayed for luciferase activity using a luciferase assay kit (Promega, Madison, Wis.) on GloMax®-Multi+ Detection System (Promega). In second cycle assays, supernatants were collected from all conditions of the first cycle at 96 hpi and used for infection of fresh HFFs in 96-well-plates. Luciferase activity was measured 72 h following second cycle infection. For HSV1-KOS/Dlux/oriS, a luciferase assay was performed at 24 hpi. Plaque assays were performed with clinical isolates of HSV2 and HCMV Towne. HFFs were seeded at $3 \times 10^6$ cells/plate in 12-well plates and infected 24 h later with HSV2 at 200 PFU/well. For HCMV, HFFs were seeded at 0.5 or 2 million cells/plate in a 12-well plate and infected 24 hours later at 100 PFU/well. Following virus adsorption (60 min and 90 min for HSV and HCMV, respectively), virus was aspirated, and DMEM containing 4% fetal bovine serum (FBS) with (for HSV) or without (for HCMV) 0.5% carboxymethyl-cellulose, were added with the compounds at indicated concentrations into triplicate wells. After incubation at 37° C. for 10 days (for HCMV) or 2 days (for HSV), the overlay was removed and plaques were counted after crystal violet staining.

Generation of Drug Resistant Virus.
Screening of drug resistant virus was performed as reported. Two million cells were plated on a 6-well plate and infected with HCMV (MOI 0.05). After 90 min cells were washed with PBS and 10 nM of emetine or 0.5 µM of GCV were added. The cells were maintained in DMEM with 4% FBS until plaques were observed. The supernatants from these plates were used to infect fresh HFFs in a 6-well plate and each time drug concentration was increased by two fold. The cells were passaged 5 times until a final drug concentration of emetine (2.4 µM) and GCV (10.5 µM). DNA extracted from supernatants collected at the last stage was used for UL97 sequencing.

Cell Viability.
Cells were seeded in 96-well microplates, treated with various concentrations of emetine and incubated at 37° C.

for 3 days. Cell viability was determined by an MTT [3-(4,5-dimethyl-2-thiazolyl)-2,5-diphenyl-2H-tetrazolium bromide]-based colorimetric assay following manufacturer's instructions (Sigma-Aldrich). For each cell type used for virus infection and drug treatment, the MTT assay was performed at the same time points as the antiviral assay.

Drug Combination.

The combined inhibitory effect of compounds on HCMV replication was determined in infected HFFs. A dose response curve was first generated for each compound; the $EC_{50}$ and slope were calculated. For drug combination, the concentrations of each drug were twice its $EC_{50}$ followed by 2-fold serial dilutions. The Bliss model was used for quantification of the effect of two compounds on HCMV replication (40). In this model, drug combination represents the product of two probabilistically independent events as described in the following equation (41):

$$F_{U1+2} = F_{U1} \cdot F_{U2} = \frac{1}{1+\left(\frac{D_1}{EC_{50(1)}}\right)^{m_1}} \cdot \frac{1}{1+\left(\frac{D_2}{EC_{50(2)}}\right)^{m_2}}$$

Where D is the drug concentration, m is the slope, and $EC_{50}$ is the effective concentration resulting in 50% virus inhibition. The combined effect of two inhibitors ($F_U$, fractional unaffected) is computed as the product of individual effects of the two inhibitors, $F_{U1}$ and $F_{U2}$. If the ratio of observed fold inhibition divided by the expected fold inhibition is greater than 1, the compounds are synergistic. If the ratio is less than 1, the combination is considered antagonistic, and if it equals to 1 the combination is additive.

Add on and Removal Studies.

HFFs were infected with pp28-luciferase Towne, and at 0, 6, 12, 24, 36 and 48 hpi, the medium was replaced with a medium containing emetine or GCV. For time-of-removal studies, the medium containing the compounds was removed at 0, 6, 12, 24, 36 and 48 hpi, cells were washed three times with phosphate-buffered saline (PBS), and drug-free medium was added. Luciferase activity was determined at 72 hpi.

Immunofluorescence.

Emetine, GCV and a human-specific Toll-like receptor 9 (TLR9) ligand, CpG 2006 (42), were used to determine inhibition of virus entry. Compounds were diluted in serum-free medium and added to HFFs seeded on chamber slides 24 h prior to infection. After infection and treatment, cells were fixed, permeabilized, and air-dried. Cells were then incubated with mouse monoclonal anti-pp65 antibody at 37° C. in humidified chambers for 1 h, washed three times with 0.1% Tween 20 in PBS (PBST), incubated with rhodamine conjugated anti-mouse IgG (Sigma Chemical Co) at 37° C. in humidified chambers for 1 h, and washed with PBST (0.1% Tween 20). A drop of mount oil containing DAPI (4,6-diamidino-2-phenylindole) (Santa Cruz) was added to the slides before visualization with a Nikon Eclipse E-800 fluorescence microscope.

Pharmacokinetics and CMV Inhibition in Mice.

For the PK study, male BALB/c mice (n=3 per time point) were treated with a single oral administration of 1 mg/kg emetine or a single intraperitoneal dose of 0.1 mg/kg. The dosing solution was prepared in saline with a dosing volume of 10 mL/kg. Blood and tissue samples including liver, lung and spleen were collected at 0, 0.083, 0.25, 0.5, 0.75, 1, 2, 3, 4, 7, 24, 30, 48, 72 and 96 hr. Emetine concentration in plasma and tissue homogenates was determined by LC-MS/MS. Pharmacokinetic parameters ($C_{max}$, $T_{max}$, AUC and $t_{1/2}$) were calculated with a non-compartmental approach using the Pharsight WinNonLin software (Ver. 6.4). The experimental procedures were approved by the Animal Care and Use Committee of Division of Veterinary Resources, NIH.

For infection experiments BALB/c mice, 4-6 weeks old, 18-22 g, were purchased from Harlan Laboratories (Indianapolis, Ind.). The experimental procedures were approved by the Animal Care and Use Committee of Johns Hopkins University. After 2-3 days of adaptation to the housing environment, mice were randomly divided into five groups as follows: control (5 mice), infected (10 mice), infected+ emetine, 0.1 mg/kg (10 mice), infected+emetine 1.0 mg/kg (10 mice) and infected+GCV 10 mg/kg (10 mice). Mice were infected intraperitoneally with $10^6$ PFU/mice (0.1 mL in 0.8% saline). Control mice received 0.1 ml of saline intraperitoneally. One day after infection, mice were treated with emetine (once daily oral dosing, every three days) or GCV (twice daily intraperitoneally dosing). Control and infected mice received equivalent volumes of saline. A total of three doses of emetine and ten doses of GCV were administered. Mice were sacrificed at day 14 after infection. Blood samples were collected by cardiac puncture. Salivary glands and liver were harvested and stored at −80° C. until further use. Organs were homogenized in DMEM with 4% FBS at a final concentration of 100 mg/mL. Two million MEFs were seeded into 24 well plates. From each sample, 5% of the salivary gland homogenate or 10% of the liver homogenate was used for infection of MEFs in triplicates. Plaques were counted after three days. Viral load was measured in whole blood at day 14 by quantitative real-time PCR of the glycoprotein B (gB) gene. DNA was extracted using the DNA blood mini kit (Qiagen). The gB primers were: F: 5' AGG GCT TGG AGA GGA CCT ACA 3' (SEQ ID NO:1); R: 5' GCC CGT CGG CAG TCT AGT C 3'(SEQ ID NO:2) (43).

RNA Isolation and Real Time Quantitative Reverse Transcriptase (qRT) PCR.

Total RNA was isolated from cultured cells using RNeasy Mini kit (Qiagen, Georgetown, Md.) according to manufacturer's instructions. RevertAid first strand cDNA synthesis kit (Fermentas life sciences, Cromwell Park, Md.) was used to synthesize first strand cDNA from total RNA using oligo-dT primers. Negative reverse-transcriptase (−RT) reactions were included to ensure the specificity of qRT-PCR reactions. Synthesis of first strand cDNA from mRNA template was carried out at 42° C. for 1 h. Quantitative RT-PCR (qRT-PCR) was performed using specific primers for p21 (F: 5' TGG AGA CTC TCA GGG TCG AAA 3' (SEQ ID NO:3); R: 5' CGG CGT TTG GAG TGG TAG AA 3') (SEQ ID NO:4) and SYBR green (Fermentas life science) with two-step cycling protocol (95° C. for 15 s, 60° C. for 1 min). Reactions were performed in triplicates and GAPDH (F: 5' CGG AGT CAA CGG ATT TGG TCG TAT 3' (SEQ ID NO:5); R: 5' AGC CTT CTC CAT GGT GAA GAC 3' (SEQ ID NO:6)) was used as the internal control.

SDS-Polyacrylamide Gel Electrophoresis and Immunoblot Analysis.

Cell lysates were quantified for protein content using bicinchoninic acid (BCA) protein assay kit (Pierce Chemical, Rockford, Ill.). Equivalent amount of proteins were used for Western blot analysis as described previously. Protein bands were visualized by chemiluminescence using Western Blotting Luminol Reagent (Santa Cruz Biotechnology, Santa Cruz, Calif.). The following antibodies were used for detection of HCMV proteins: mouse anti-IE1 and IE2, (MAb810); mouse anti-UL44 (Santa Cruz biotechnology Santa Cruz, Calif.); mouse monoclonal anti-pp65 (Vector laboratories, Burlingame, Calif.); mouse monoclonal anti-β-actin antibody (Millipore, Billerica, Mass.); rabbit polyclonal anti-RPS14 and mouse monoclonal anti-MDM2 (AbCam, Cambridge, UK); mouse monoclonal anti-p53 (Santa Cruz, Calif.); horseradish peroxidase (HRP)-conjugated goat anti-rabbit IgG (Cell Signaling); and HRP-conjugated sheep anti-mouse IgG, (GE Healthcare, Waukesha, Wis.). For detection of co-immunoprecipitated proteins, protein A-HRP conjugate (Cell Signaling Technologies, Beverly, Mass.) was used as secondary antibody to eliminate the interfering IgG bands.

Transient Transfections.

HEK-293 cells seeded into 10 cm petri dishes were transfected with HCMV plasmid encoding IE1 and IE2 (pRL45) plasmid, 1 μg/dish, using Lipofectamine 2000 in serum free medium. After 6 h, 10% FBS containing media was added along with 10 μM of MG132. Following overnight incubation emetine (75 nM) or GCV (5 μM) were added for 4 h. Cells were then harvested to prepare lysates for IP.

Co-Immunoprecipitation (IP) and Immunoblotting.

Non-infected, infected or emetine-treated HFFs were treated with MG132 (10 μM) for 12 h. Cells were harvested after 24 hpi and lysed with IP buffer containing 150 mM NaCl, 50 mM Tris pH 7.5, 2 mM EDTA, 0.5% TritonX-100 and 0.5% NP-40-40. 1 mg of lysate was precleared with bead slurry for 30 min. The precleared lysates were incubated with anti-MDM2 (2 μg) antibody overnight. The antibody complexes were isolated using protein A/G beads (Santa Cruz), washed three times with 50% IP buffer. The immunoprecipitate-protein A/G beads were boiled in SDS sample buffer, and the supernatant was analyzed on SDS-PAGE gels after immunoblotting as described previously. 1% of the cell lysate used for IP was loaded on gels as 'Input'. Reverse IPs were performed by pulling down the precleared lysates with either anti-p53 antibody or anti-RPS14 antibody and detected with MDM2. In other experiments, lysates were harvested 72 hpi and pulled down with anti RPS14 antibody followed by detection with anti-RPS14 antibody or mouse anti-Ubiquitin antibody (Santa Cruz). In other experiments, transfected or treated HEK293 cell lysates were pulled-down with anti-IE2 antibody and detected with anti-MDM2 antibody and vice-versa for reverse IP.

Confocal Microscopy.

Two million cells were plated on a chamber slide followed by infection with HCMV and treatment with emetine or GCV for 24 or 72 h. Cells were fixed with 3.7% paraformaldehyde for 20 min at room temperature, permeabilized with ice cold methanol for 10 min at −20° C. and blocked with 5% bovine serum albumin in 0.5% Tween-20 for 20 min at room temperature. Cells were incubated with primary antibodies at 4° C. overnight, washed and incubated with fluorescently labeled secondary antibodies for 2 h at 37° C. Fluorescence microscopy was performed by using a confocal laser scanning microscope (Nikon EZ C1 confocal microscope). All images were captured at 60× magnification and processed under identical conditions with constant parameters (including scan speed and excitation and emission wavelengths) using Nikon EZ C1 software.

Lentivirus-Mediated Knockdown (KD) of RPS14.

Human TRC lentiviral shRNA constructs (Sigma-Aldrich) were used for RPS14 knockdown (KD) in HFFs. Four clones (Clone ID: TRCN0000008641-4) targeting different regions of RPS14 mRNA were tested for KD efficiency, and the clone with the best KD efficiency was selected to generate stable cell lines. TRC non-targeting control plasmid was used to rule out non-specific effects of shRNA constructs. Individual shRNA constructs were packaged using lentivirus as described (46). Briefly, 21 μg of gag/pol, 7 μg of vesicular stomatitis virus glycoprotein, and 7 μg of shRNA plasmids were transfected into HEK293 cells using Lipofectamine. After 48 h the packaged lentivirus particles were concentrated from the medium. The supernatant was filtered and centrifuged at 1750 g for 30 min at 4° C. in Amicon Ultra (Ultracel 100 k, Millipore). After centrifugation, 2 ml of cold PBS was added and the tubes were centrifuged again for 20 min at 4° C. The concentrated virus was stored at −80° C. until used. Lentivirus particles containing shRNA were transduced into HFFs. $2.0 \times 10^6$ cells were plated onto T-75 flask and 50 μl of concentrated virus and hexadimethrine bromide (final concentration, 8 μg/ml) were added to the cells, and incubated for 24 h. Following transduction puromycin (2 μg/ml) was added to select for stably transduced cells. Control HFFs and RPS14 KD HFFs were counted and equal number of cells was plated into each well prior to infection or treatment.

Statistical Analysis.

Statistical significance was assessed with GraphPad Prism 5.0 software. Data are presented as mean±SD (n≥3). Student's t test was used to determine whether the mean of two groups are significantly different. In all analyses, two sided P values were used, and P<0.05 was considered statistically significant. For animal studies, one way Anova was used to determine significance.

Results

Emetine Inhibits HCMV and HSV Replication at nM Concentrations.

Figures 1C, 1D:
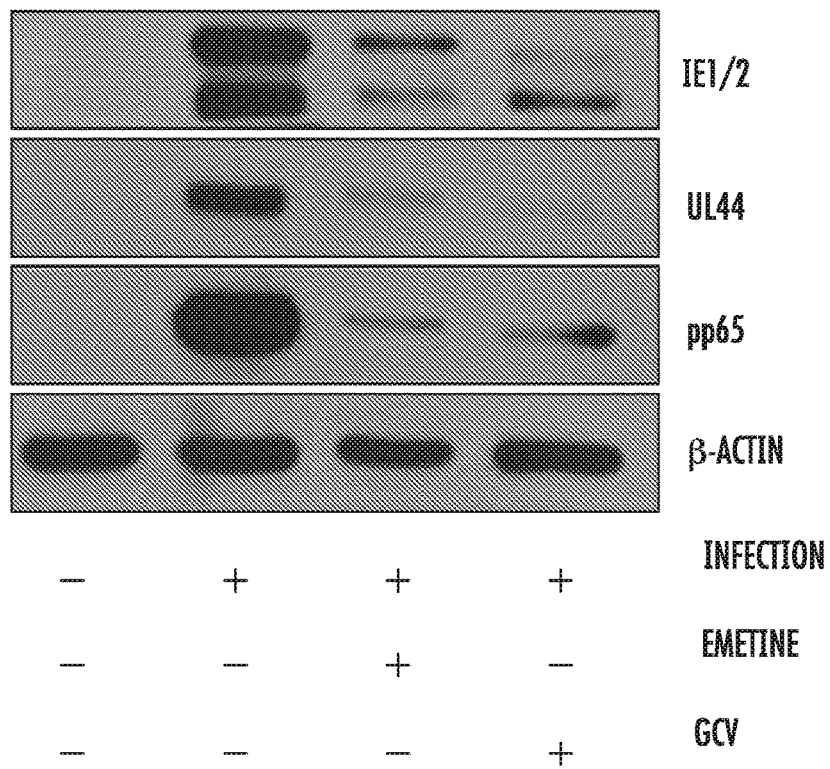
Figure 1E:
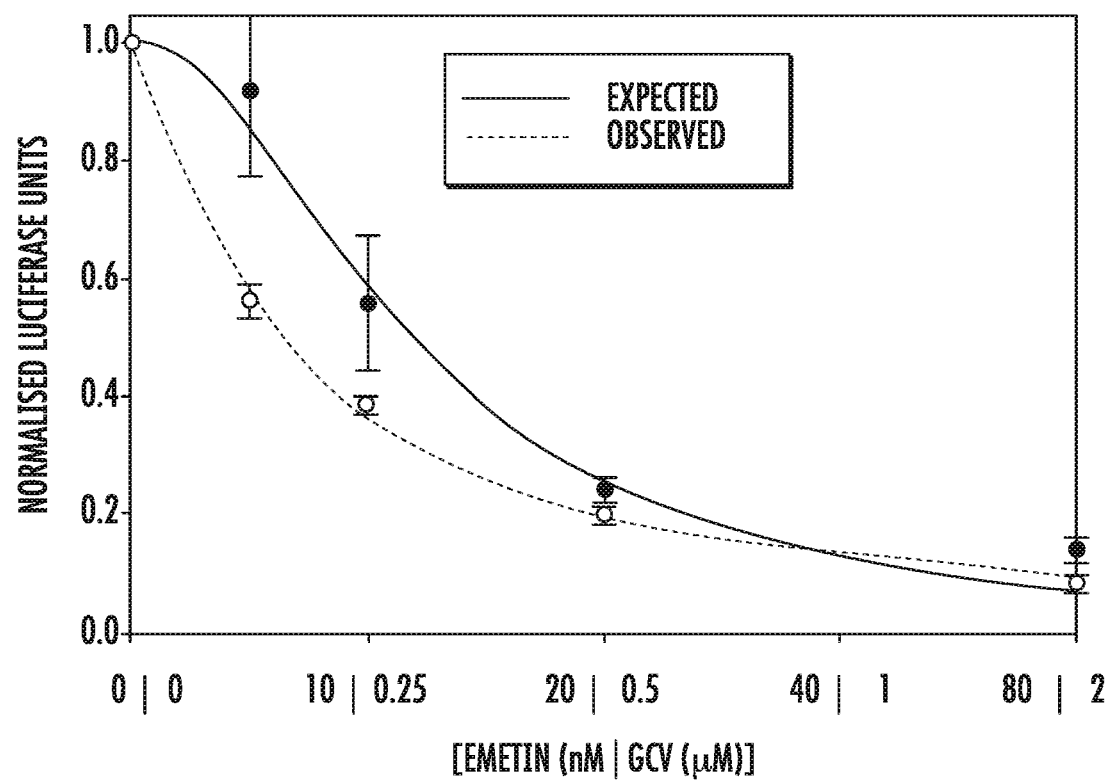

Screening of the LOPAC library of 1,280 pharmacologically active compounds using a pp28-luciferase HCMV Towne identified emetine as a potential HCMV inhibitor. A dose response curve was generated to confirm the anti-HCMV activity of emetine. The $EC_{50}$ of emetine against pp28-luciferase HCMV Towne was 40±1.72 nM, and the $CC_{50}$ in non-infected HFFs—8±0.56 μM, yielding a selectivity index (SI) of 200. The Hill slope of the concentration-response curve was 3.1, indicating a robust virus inhibition at higher concentrations (FIGS. 1A and B). A GCV-resistant pp28-luciferase HCMV was also inhibited by emetine. Inhibition of HCMV by emetine was further confirmed by plaque reduction assay (FIG. 1C). The activity of emetine against HSV-1 and HSV-2 was determined by luciferase and plaque assay, respectively. HSV-1 and HSV-2 were also inhibited by emetine in HFFs at nM concentrations (FIG. 1C). The expression of HCMV proteins IE1/2, UL44 and pp65 was significantly reduced by emetine at 72 hpi (hours post infection) (FIG. 1D). Combination of emetine and GCV showed synergistic virus inhibition as compared to the individual effect of each drug, as determined by the Bliss model (FIG. 1E). These results indicate significant inhibitory effect of emetine against HCMV, GCV-resistant HCMV and HSVs at nM concentrations, much lower than those reported for its' translation inhibition.

Emetine Inhibits HCMV Replication after Entry but Before Initiation of DNA Replication.

Figure 2A:
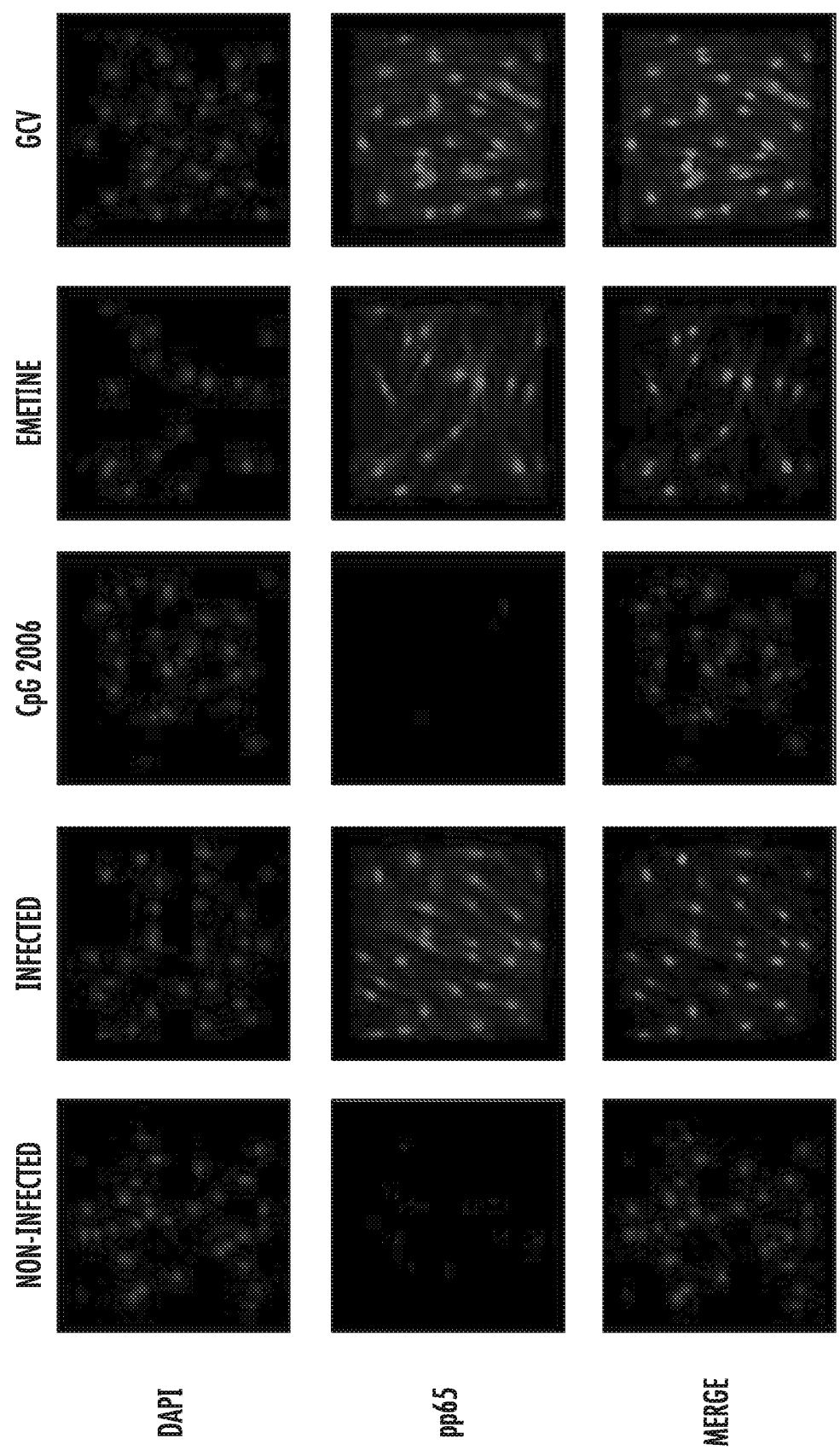
FIGS. 2A-2C: Emetine is an early inhibitor of HCMV replication. A) Emetine does not inhibit HCMV entry. Cells were treated with emetine (75 nM), GCV (10 μM), and CpG 2006 (10 μM) 24 h prior to infection. Cells were infected with HCMV and treated with compounds for 90 min. Immunofluorescence staining was performed with mouse monoclonal anti-pp65 antibody. The fluorescence of rhodamine anti-mouse IgG and DAPI was visualized and merged using a Nikon Eclipse E-800 fluorescence microscope. B) Emetine has an early activity against HCMV. Cells were infected with pp28-luciferase HCMV Towne, and compounds were added at 0, 6, 12, 24, 36, and 48 hpi (Add on). Luciferase activity was measured at 72 hpi. C) Cells were infected with pp28-luciferase HCMV Towne and treated with compounds immediately after virus adsorption. Compounds were removed at 0, 6, 12, 24, 36, and 48 hpi (Removal). Luciferase activity was measured at 72 hpi. Data represent mean±SE of triplicate determinations from a representative of two independent experiments.
Figure 2B:
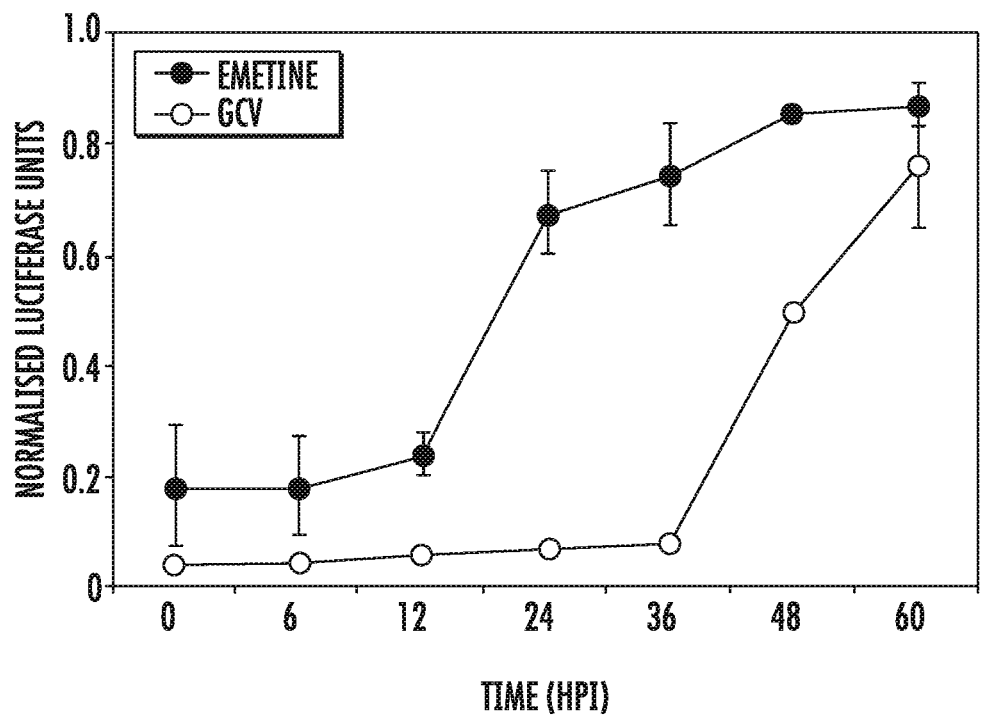
Figure 2C:
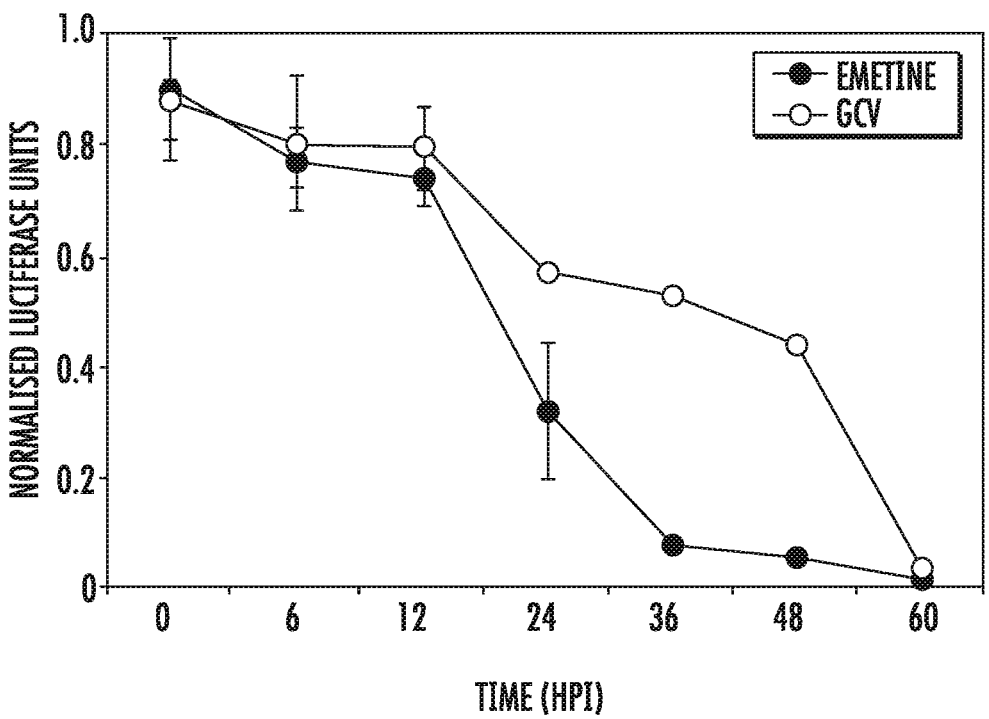

To determine the timing of HCMV inhibition by emetine virus entry and add-on and removal assays were performed. Using immunofluorescence assay for pp65, neither emetine nor GCV inhibited viral entry, but CPG 2006 (a TLR9 ligand), used as positive control, did (FIG. 2A). In an add-on and removal assay emetine or GCV were added or removed at 0, 6, 12, 24, 36, 48 and 60 hpi, and luciferase activity was measured at 72 hpi. Addition of emetine after 12 h resulted in its loss of activity against HCMV replication (FIG. 2B, p<0.0001). The removal assay revealed that emetine was required for at least 24 h to fully inhibit HCMV (FIG. 2C, p<0.05)). These results suggest that HCMV inhibition occurred during the immediate-early to early stages of HCMV replication.

Pharmacokinetic (PK) and Efficacy Studies in Mice.

Figure 3A:
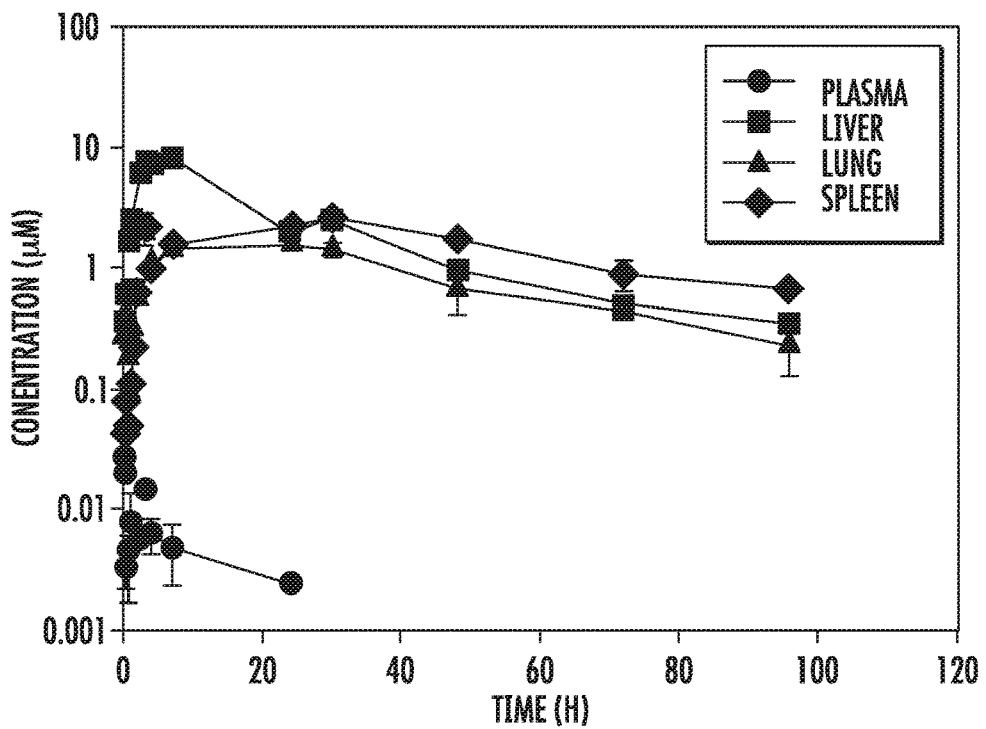
FIGS. 3A-3D: Emetine achieves high tissue concentrations and is efficacious against MCMV replication. A) In vivo pharmacokinetics of emetine. Plasma, liver, lung and spleen samples were collected at the indicated time points after single oral administration of emetine at 1.0 mg/kg in male BALB/c mice. Concentrations were measured using UPLC-MS/MS methods. B) Quantitative real-time PCR of viral gB was performed on DNA extracted from blood at day 14 post infection. Plaque assay was performed from salivary glands C) or liver D) collected at day 14 post infection. Emetine was used at 0.1 or 1.0 mg/kg every 3 days. GCV dose was 10 mg/kg/dose administered twice daily.

A PK study was conducted in male BALB/c mice after single oral administration of 1 mg/kg emetine. In vivo exposures of emetine in plasma, liver, lung and spleen were monitored after oral administration. Emetine achieved levels that exceeded its in vitro $EC_{50}$ against HCMV (FIG. 3A) and its half-life was determined to be 32 h. Another PK study of single intraperitoneal administration of 0.1 mg/kg emetine, similarly showed high drug levels in tissues and a half-life of 32 h. At the lowest Cmin, the concentration of emetine in the tissues of interest was above its in vitro $EC_{50}$ by at least 1.8 fold (FIG. 9).

Figure 3B:
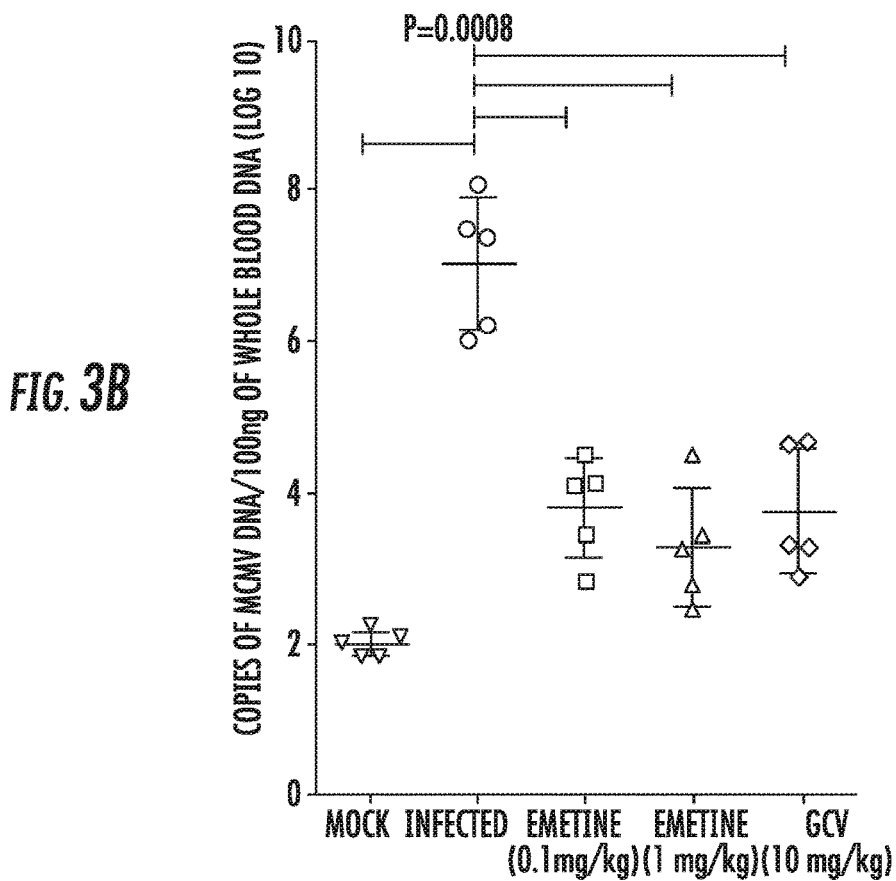
Figure 3C:
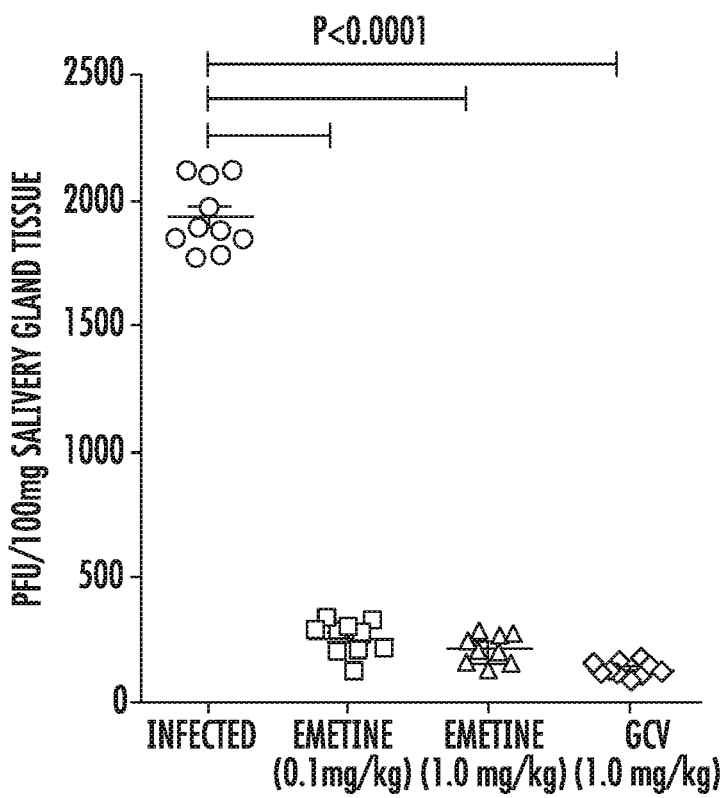
Figure 3D:
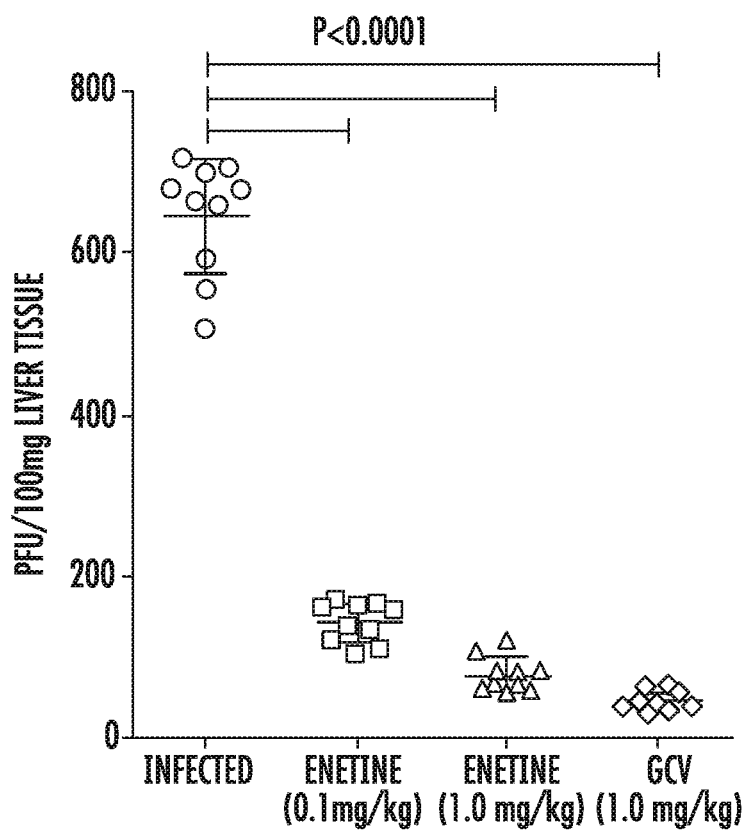

The effect of oral treatment with two doses of emetine (0.1 and 1 mg/kg) was tested on MCMV replication. BALB/c mice (3-4 week old) were infected with $10^6$ PFU/mice of tissue-culture derived MCMV intraperitoneally and treated with 0.1 or 1 mg/kg of emetine orally every three days beginning at 48 h after infection till $11^{th}$ day post infection. On the 14th day post infection, mice were euthanized, intracardiac blood was collected and tissues were harvested and assayed for MCMV replication by plaque assay. Emetine treatment resulted in 2 to 4 log 10 decrease (P<0.001) in MCMV DNA copy number in blood as compared to infected control (FIG. 3B). All treatment regimens resulted in 4 to 6 fold reduction of viral PFUs in salivary gland (FIG. 3C) and 3 to 6 fold in liver (FIG. 3D, p<0.0001)). There was no significant difference in the efficacy of the two doses of emetine used.

HCMV Inhibition by Emetine Depends on Cell Confluency at the Time of Infection.

Figure 4A:
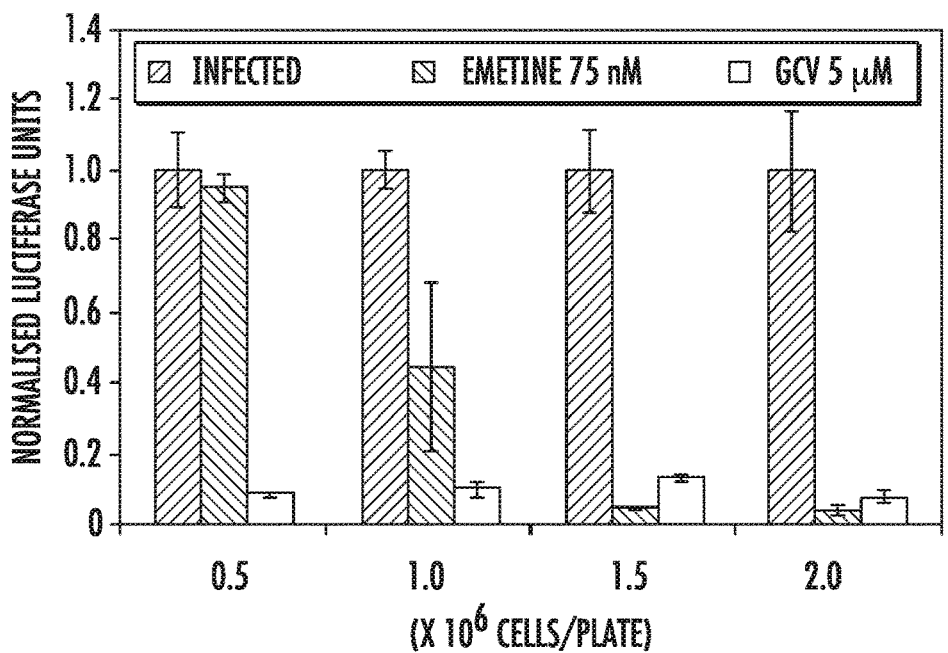
FIGS. 4A-4D: The anti-HCMV activity of emetine is reduced in cycling HFFs. A) Cells were seeded at indicated densities in a 96-well plate, infected with pp28-luciferase HCMV Towne (MOI=1) and treated with emetine (75 nM) or GCV (5 μM). Luciferase activity was measured at 72 hpi and normalized to the activity of infected untreated cells. Data represent mean±SE of triplicate determinations from a representative of two independent experiments. B) Same cell lysates as in A were collected for Western blotting at 72 hpi and expression of viral proteins UL44 and pp65 was determined. C) Supernatants from each well as in A were used to infect cells (1 million cells in a 96-well plate) in the corresponding well and luciferase activity was measured at 72 hpi. D) Cells were seeded into 12-well plates at 0.5 and 2 million cells/plate, infected with 100 PFU/well of HCMV Towne, and treated with emetine (75 nM) or GCV (5 μM). After 10 days plaques were stained with crystal violet and the number of plaques enumerated. Data shown are average of 2 wells (±SD) for a representative experiment from two different experiments.
Figure 4B:
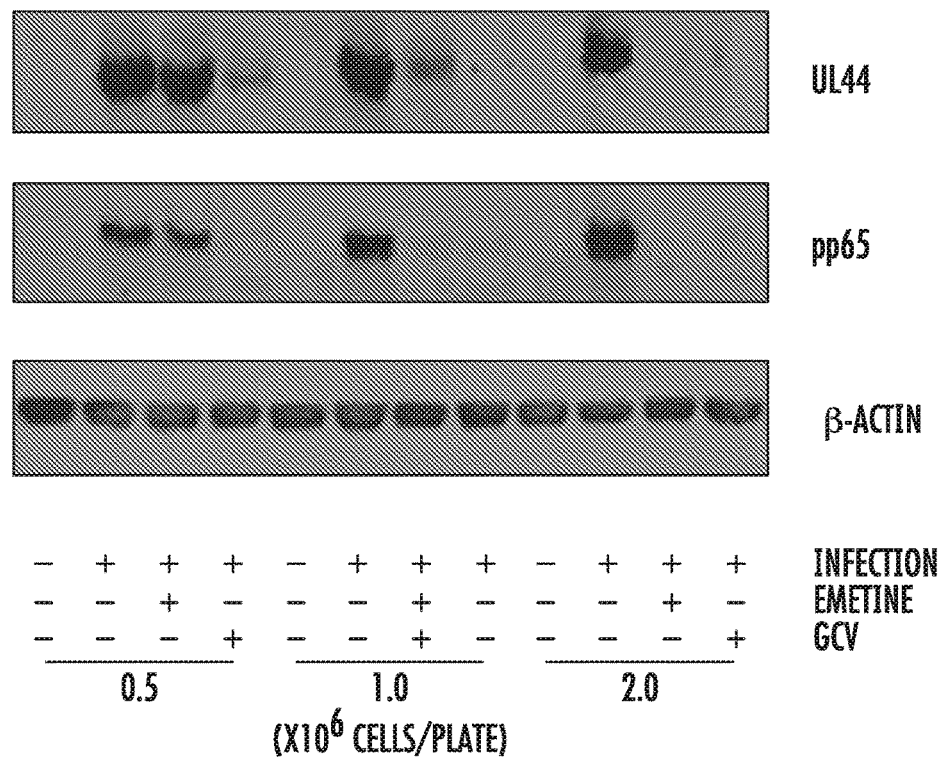
Figure 4C:
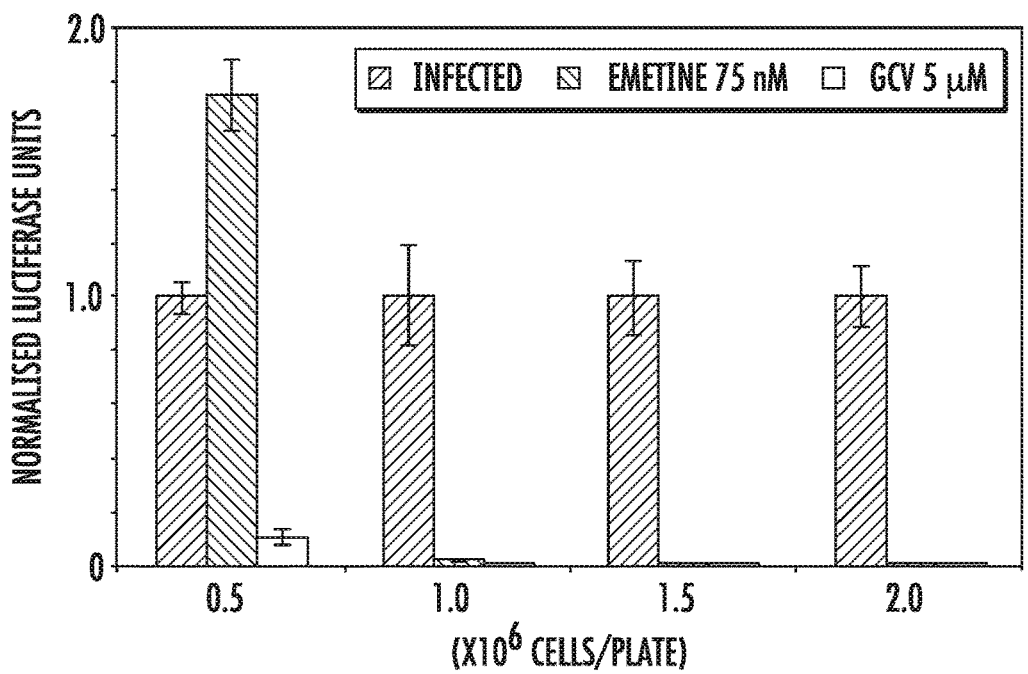
Figure 4D:
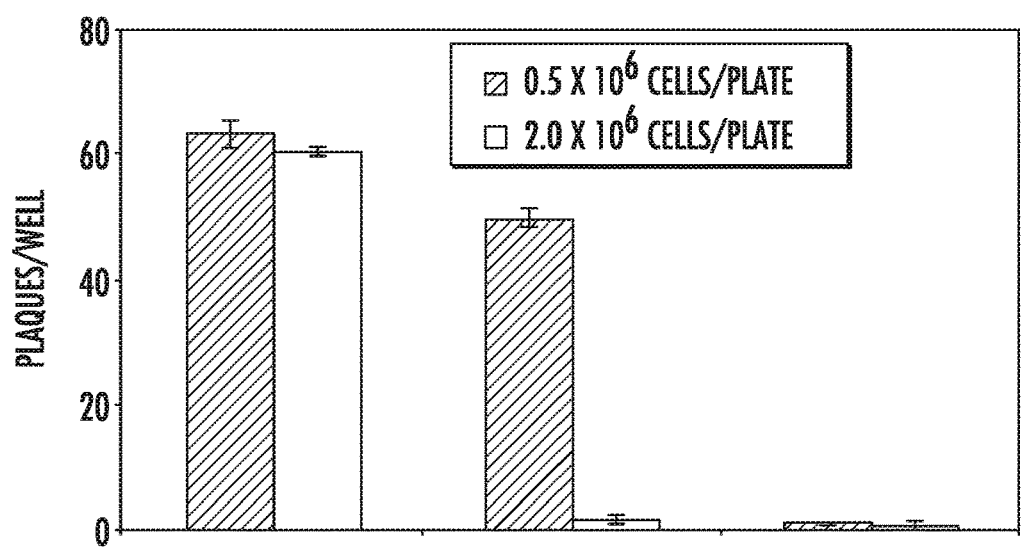

Interestingly, the same batch of emetine exhibited inconsistent activity against HCMV replication in vitro. This was not because of selection of resistant viruses, as increasing emetine concentration did not lead to reappearance of pp28-luciferase activity, while GCV did select for resistant mutants and a C607Y mutation in UL97 was confirmed by sequence analysis. The effect of cell density at the time of infection on HCMV inhibition by emetine was investigated. HFFs were seeded at cell densities ranging from 0.5-2 million cells/plate followed by HCMV infection and drug treatment. HCMV inhibition by emetine correlated with cell confluence at the time of infection; significant virus inhibition was observed only at higher cell density. The pp28-luciferase assay showed no significant reduction in normalized luciferase activity by emetine at low cell density (0.5 million/plate in 96-well plate), whereas with increased cell density more significant reduction was observed (FIG. 4A). Western blots revealed significant reduction of viral UL44 and pp65 expression with emetine at high cell density but not at a lower cell density, compared to infected untreated cells (FIG. 4B). Second cycle infection showed that in emetine treated condition there was 1.5-fold increase in pp28-luciferase activity in 0.5 million cells/plate (p>0.5), 1.5-fold reduction in 1 million cells/plate (p<0.001) and almost complete inhibition in 2 million cells/plate (p<0.001) as compared to the infected control (FIG. 4C). Plaque reduction assays showed 30 fold reduction in the number and size of plaques with emetine at 2 million cells/plate (p<0.001) as compared to 0.5 million cells/plate (p>0.05) (FIG. 4D). GCV inhibited HCMV replication irrespective of cell density (p<0.001). These results suggest that emetine activity against HCMV depends on cell cycle regulation.

Emetine Induces an Interaction Between RPS14 and MDM2.

Figure 5A:
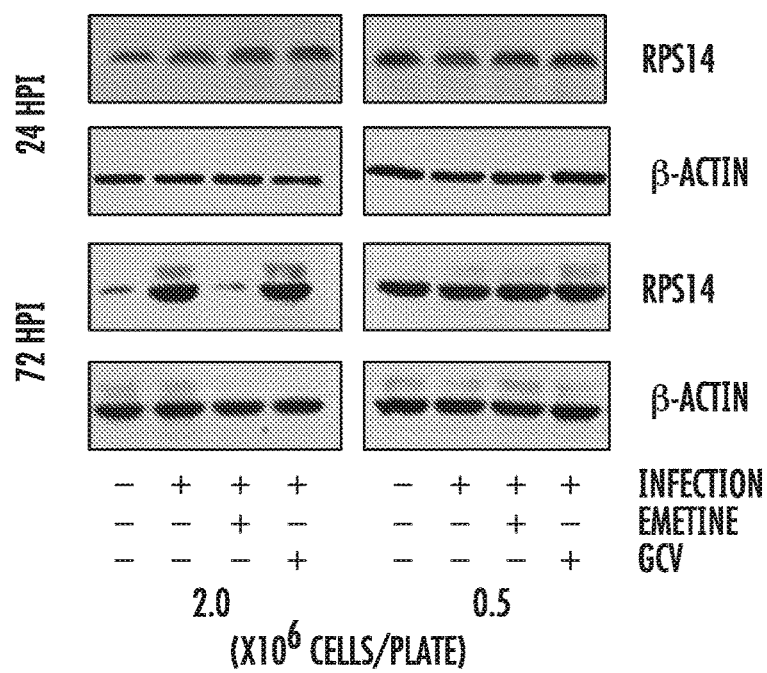
FIGS. 5A-5E: Emetine induces an interaction between MDM2 and RPS14 in infected contact-inhibited cells. A) Emetine abrogates infection-mediated overexpression of RPS14 at 72 hpi. Cells were seeded at 0.5 or 2 million cells/plate in 96-well plate, infected with Towne HCMV and treated with emetine (75 nM) or GCV (5 μM). Lysates were collected at 24 or 72 hpi for Western blotting. B) HFFs were seeded at 1 or 2 million cells/plate in a 96-well plate and treated with emetine or GCV. Lysates were collected at 72 hpi for Western blotting. C) Cells were seeded at 0.5 or 2 million/plate in 100 mm dishes, infected with Towne HCMV followed by treatment with emetine (75 nM) or GCV (5 μM) for 24 h. The proteasomal inhibitor MG132 (10 μM) was added after 12 h. At 24 hpi, lysates were collected and subjected to immunoprecipitation with anti-MDM2 followed by immunoblotting with anti-RPS14 antibody or D) In reverse IP, immunoprecipitation was performed with anti-RPS14 followed by immunoblotting with anti-MDM2 antibody E) A model showing the interaction of MDM2 and RPS14 in contact-inhibited but not in cycling cells.
Figure 5B:
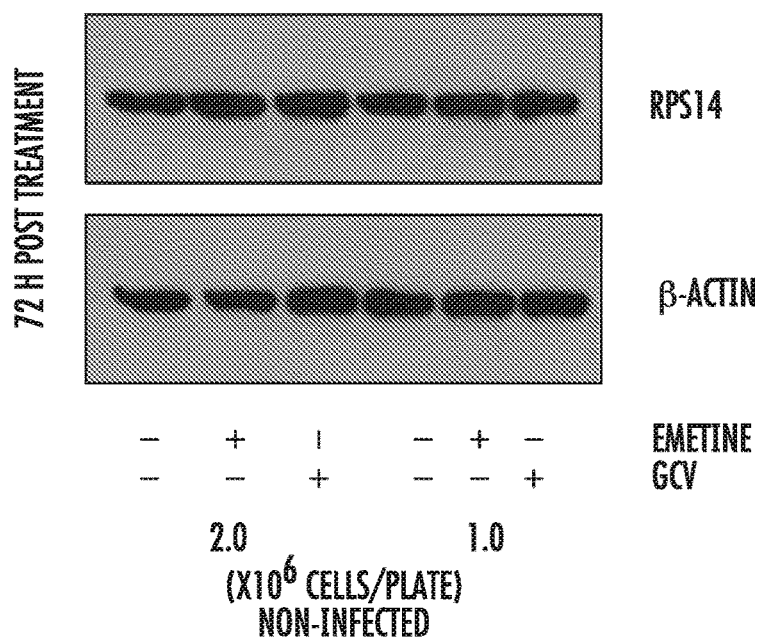

Resistance to emetine in Chinese hamster ovary cells was associated with mutations in the ribosomal protein S14 (RPS14) (10). This protein has been reported to interact with p53-MDM2, major regulators of cell cycle progression. We theorized that the RPS14-MDM2-P53 plays a role in HCMV replication and may be regulated by emetine in HCMV-infected cells. The expression of RPS14 was measured in contact-inhibited and cycling cells, infected or uninfected. HCMV induced RPS14 expression at 72 hpi in contact-inhibited cells, which was reduced with emetine treatment (FIG. 5A, left). At 24 hpi RPS14 expression was unchanged in contact-inhibited or in cycling cells (FIG. 5A, upper panel, left and right). In addition, the expression of RPS14 was unchanged in infected cycling cells (FIG. 5A, right). Irrespective of cell density, there was no change in RPS14 expression in non-infected cells (FIG. 5B). Thus, induction of RPS14 expression at 72 h and its reduction by emetine was specific to infected contact-inhibited cells. Since the anti-HCMV activity of emetine occurred at the immediate early-early time of HCMV replication, the observed changes in RPS14 expression at 72 hpi represented an outcome of an earlier event.

Figure 5C:
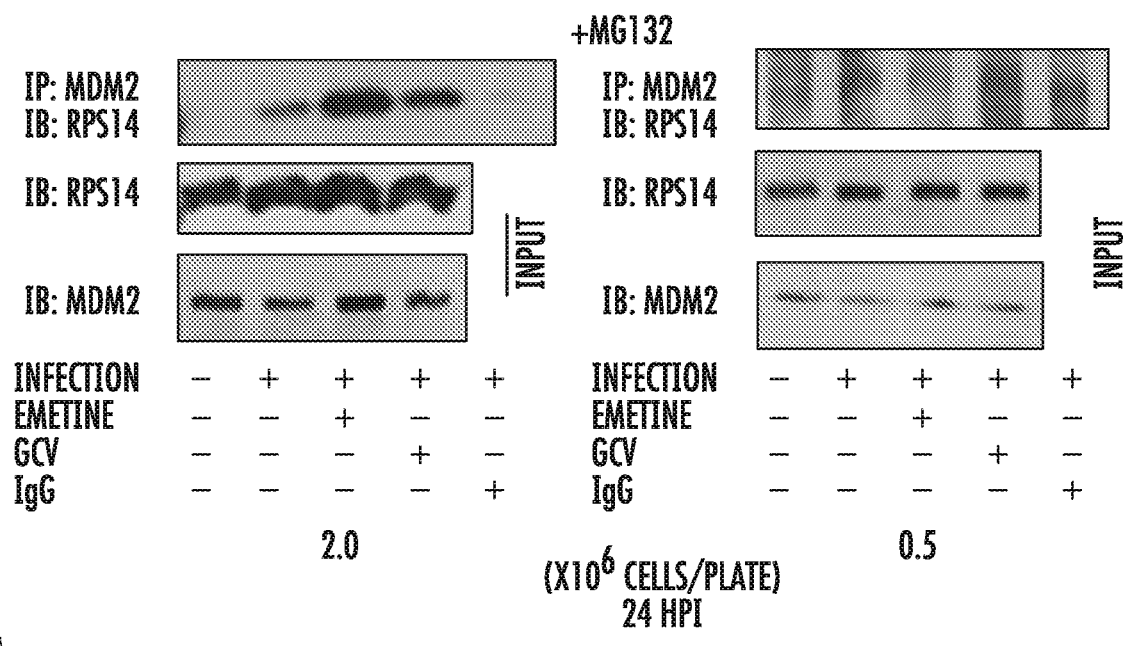
Figure 5D:
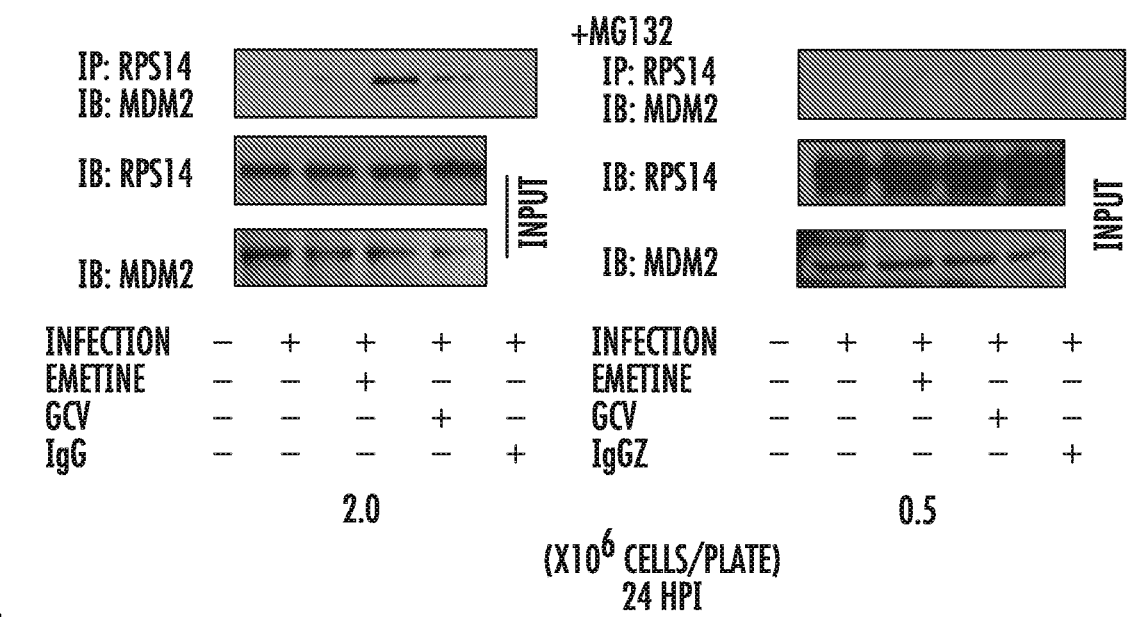
Figure 5E:
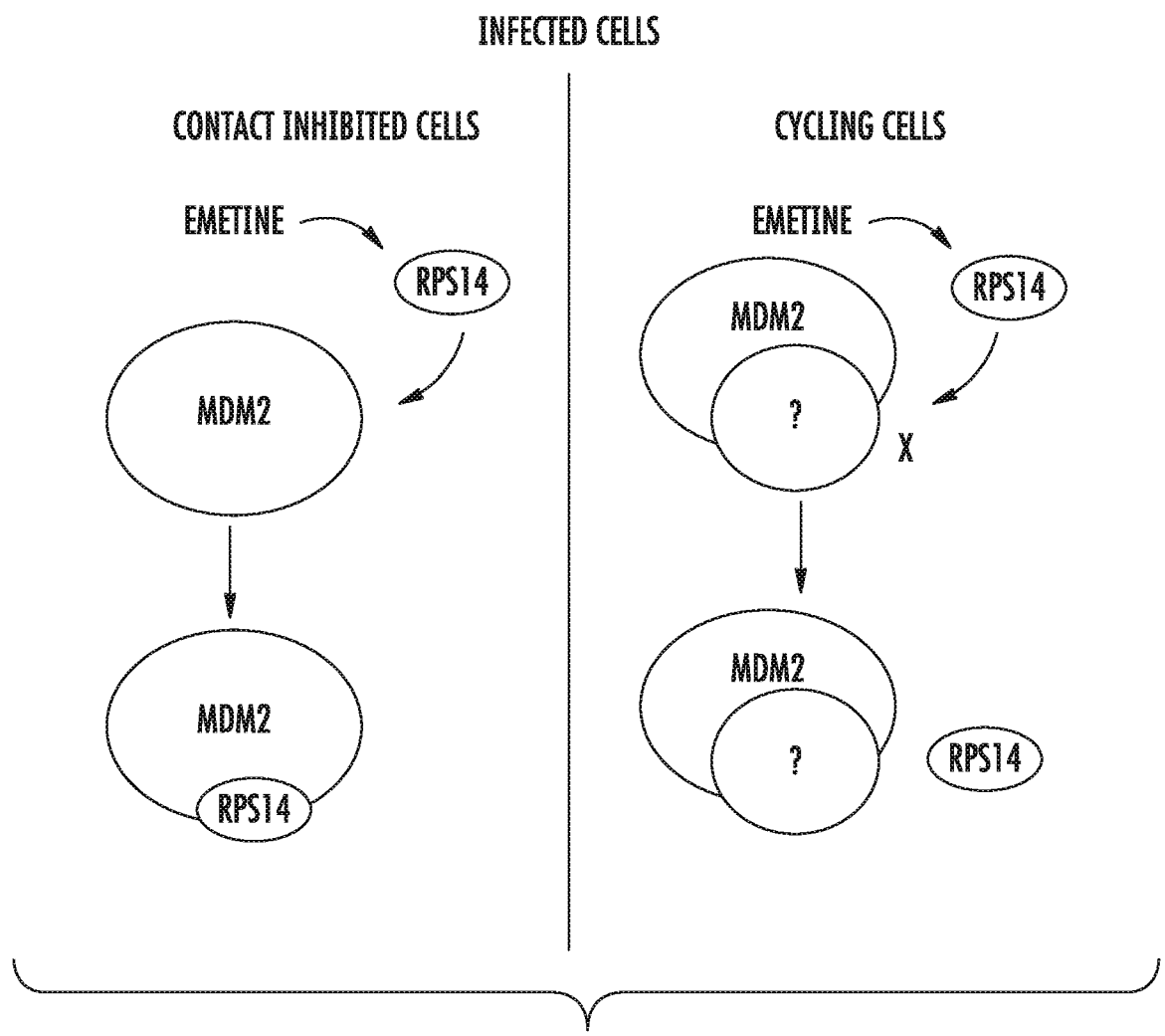
Figure 10:
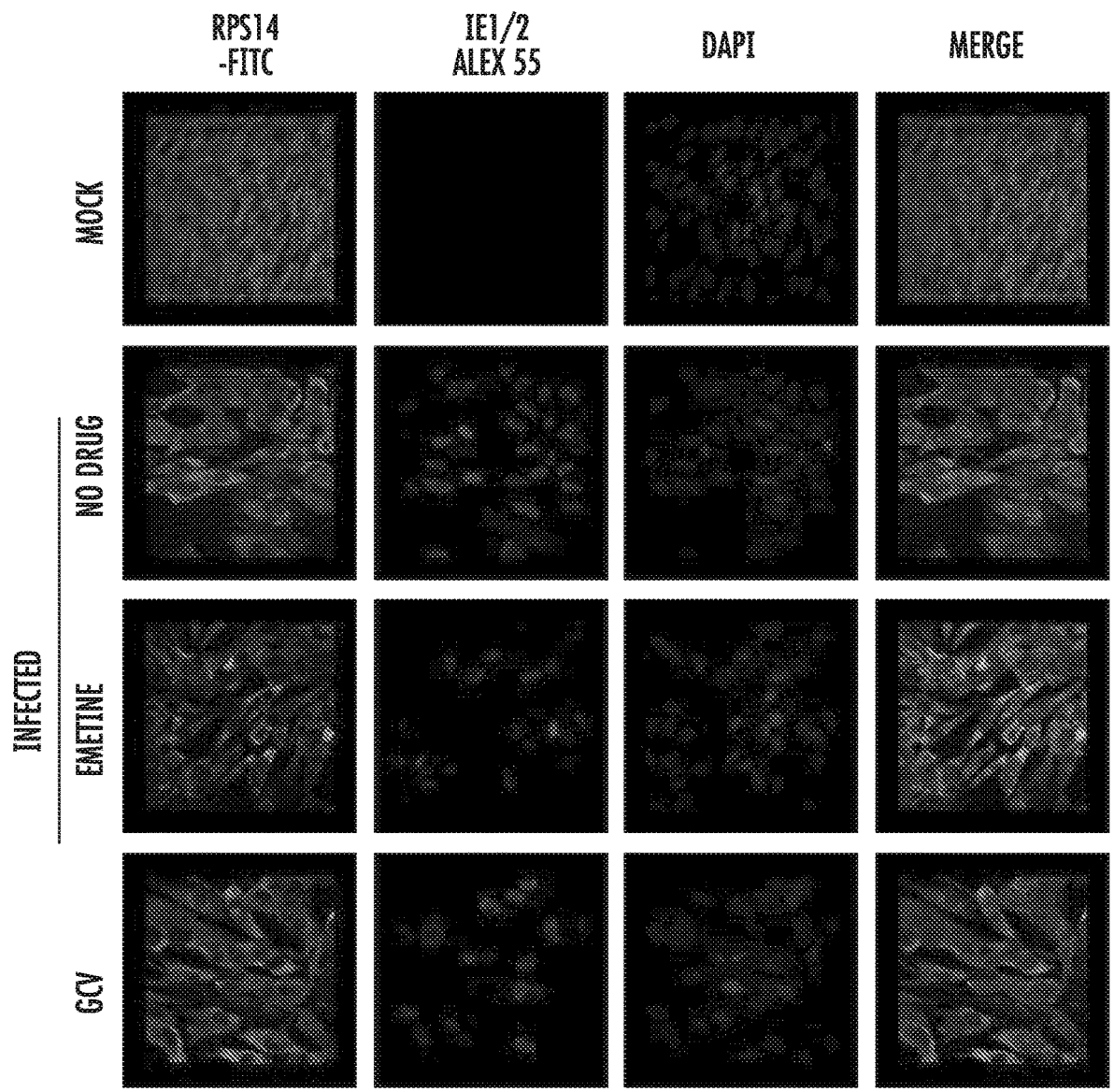
FIG. 10: Nuclear co-localization of RPS14 is not observed at 72 hpi in emetine treated cells. Cells were seeded at 2 million/plate in a 4-well chamber slide, infected and treated with emetine (75 nM) or GCV (5 µM) for 72 h. Cells were stained with IE1/2 (Alexa 555:Red) and RPS14 (FITC: Green) and nuclear DAPI. Stained slides were subjected to confocal microscopy and colocalization was studied.

RPS14 interacts with MDM2 during ribosomal stress. Therefore, the outcome of the MDM2-RPS14 interaction during infection and emetine treatment was investigated. As an E3 ubiquitin ligase, MDM2 degrades proteins to which it binds, therefore these experiments were performed in the presence of the proteasomal inhibitor, MG132. At 24 hpi emetine strongly induced the interaction between RPS14 and MDM2 in contact-inhibited cells, but not in the cycling cells (FIG. 5C). Similarly, a reverse IP showed enhanced interaction between RPS14-MDM2 in contact-inhibited cells (FIG. 5D). These results indicated that emetine induced the interaction of RPS14 with MDM2 in contact-inhibited infected cells but could not achieve the same effect in cycling cells (model depicted in FIG. 5E) or in non-infected cells (FIG. 10). The enhanced interaction was followed by reduced expression of RPS14 at 72 hpi, suggesting that MDM2 may be targeting RPS14 for degradation in infected cells.

Emetine Induces the Translocation of RPS14 into the Nucleus and Targets it for ubiquitination and Degradation.

Figure 6A:
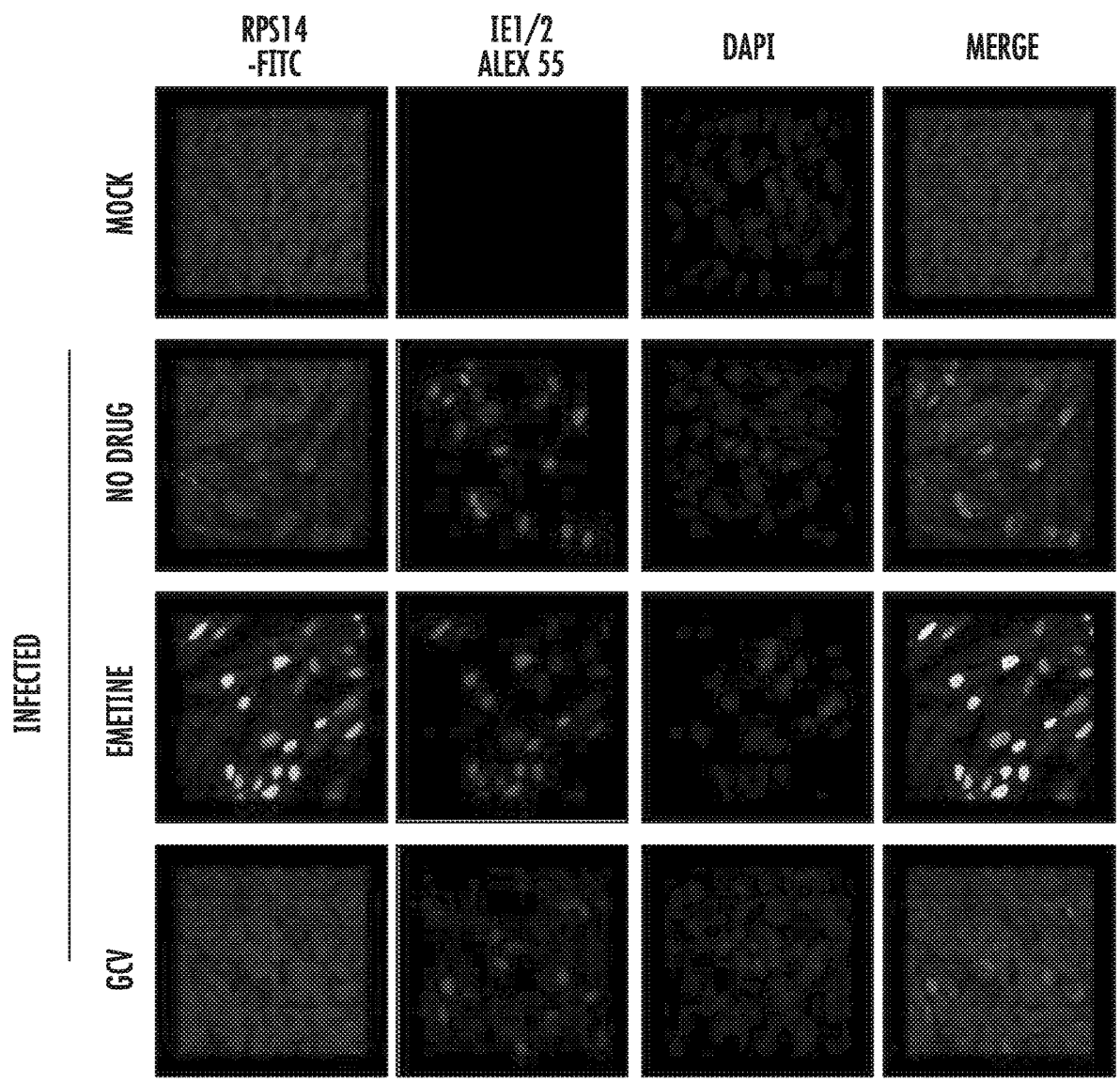
FIGS. 6A-6B: Emetine induces early nuclear translocation of RPS14 followed by late cytoplasmic relocalization and degradation. A) Cells were seeded at 2 million/plate in a 4-well chamber slide, infected and treated with either emetine (75 nM) or GCV (5 M) for 24 h. Cells were stained with IE1/2 (Alexa 555:Red) for evidence of infection and RPS14 (FITC: Green) and nuclear DAPI. Stained slides were subjected to confocal microscopy and colocalization was studied. B) Cells were seeded at 0.5 or 2 million/plate in 100 mm dishes, infected with Towne HCMV followed by treatment with MG132 (10 μM) along with emetine (75 nM) or GCV (5 M) for 72 h. Lysates were collected at 72 hpi and subjected to immunoprecipitation with anti-RPS14 followed by immunoblotting with anti-RPS14 antibody or immunoprecipitation with anti-RPS14 antibody followed by immunoblotting with anti-Ubiquitin antibody.
Figure 6B:
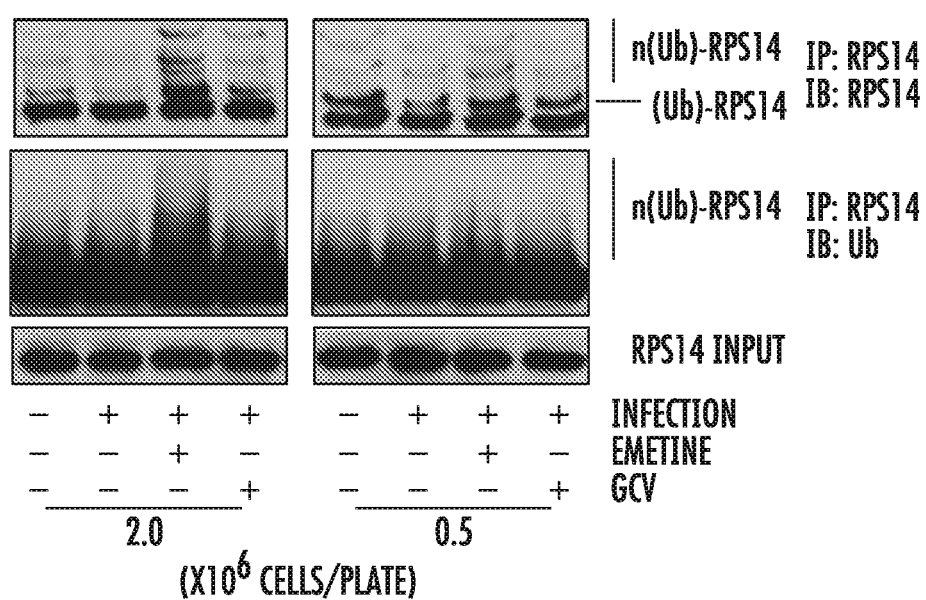
Figure 11A:
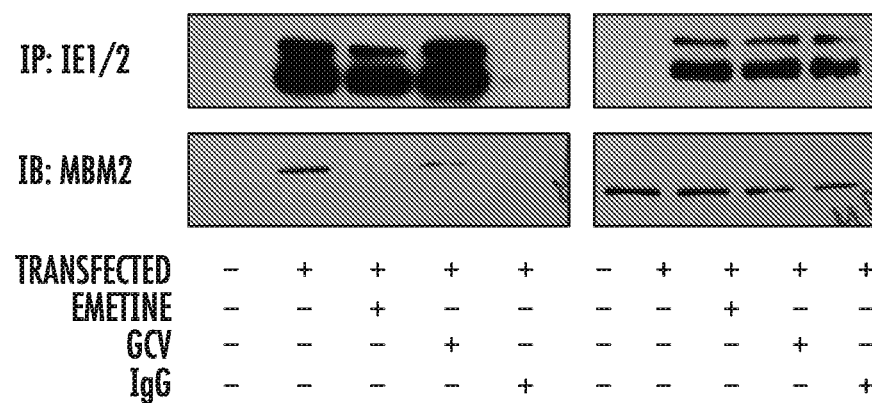
FIGS. 11A-11B: Emetine disrupts MDM2-IE2 interaction. A) HEK293 cells were seeded in 100 mm dishes and transfected with pRL45 plasmid, followed by treatment with MG132 (10 µM) for 12 h. Emetine (75 nM) or GCV (5 µM) were added for 4 h. Lysates were then subjected to immunoprecipitation with anti-IE1/IE2 antibody followed by immunoblotting with anti-MDM2 antibody or B) Reverse IP was performed with anti-MDM2 antibody followed by immunoblotting with anti-IE1/IE2 antibody.
Figure 11B:
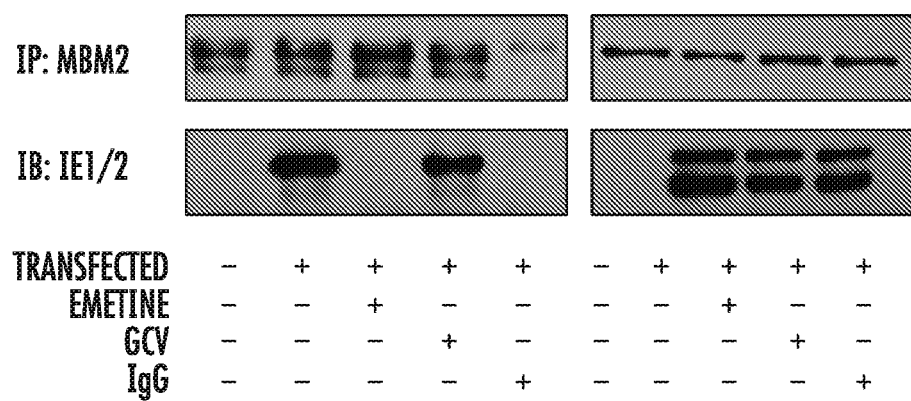

To interact with MDM2, we predicted that RPS14 would translocate into the nucleus. Using confocal microscopy, RPS14 was located in the cytoplasm of uninfected or infected cells. Emetine treatment induced RPS14 translocation into the nucleus at 24 hpi. Infected cells were identified by IE1/2 staining (FIG. 6A). Since in emetine treated contact-inhibited cells, RPS14 expression was decreased at 72 hpi (FIG. 5A), while a strong interaction with MDM2 was observed in the presence of MG132 at 24 hpi (FIG. 5C, D) we conjectured that RPS14 may be targeted for degradation. MG123-treated samples were pulled-down with RPS14 and detected with either anti-RPS14 or anti-Ubiquitin antibody. In both cell densities, RPS14 ubiquitination decreased with infection. However, only in contact-inhibited cells, emetine increased ubiquitinated RPS14 (FIG. 6B). In agreement with RPS14 ubiquitination, at 72 hpi, there was almost no nuclear localization of RPS14 in infected emetine treated cells, indicating that emetine targets RPS14 for ubiquitination and degradation (FIG. 11). Taken together, emetine treatment results in early RPS14 translocation into the nucleus of infected cells followed by its relocalization into the cytoplasm for ubiquitination and degradation, ultimately resulting in decreased RPS14 expression at 72 hpi (FIG. 5A, left).

Emetine Disrupts HCMV-Mediated MDM2-p53 Interaction.

Figure 7A:
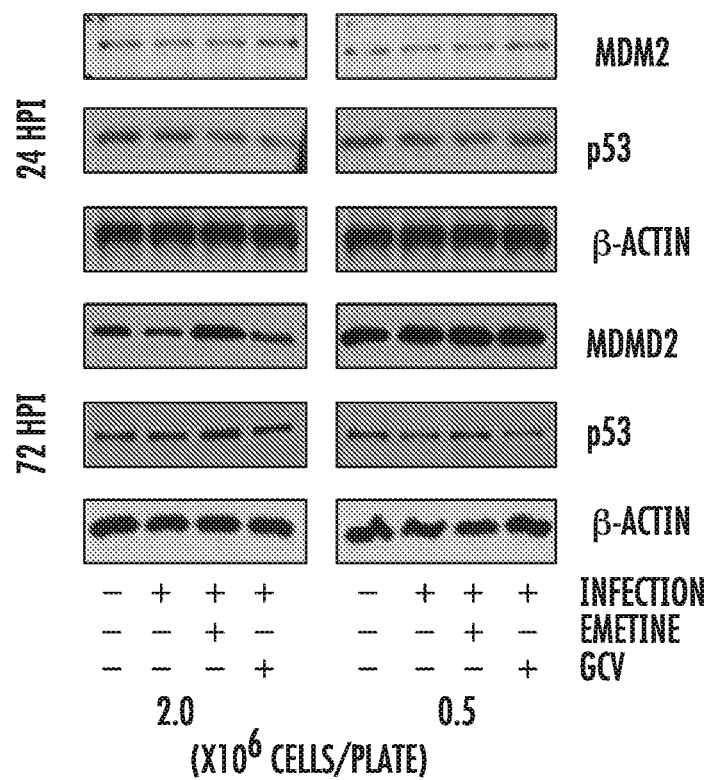
FIGS. 7A-7F: Emetine disrupts HCMV mediated MDM2-p53 complex. A) MDM2 and p53 expression increases with emetine treatment. Cells were seeded at 0.5 or 2 million cells/plate in 96-well plate, infected with HCMV Towne followed by treatment with emetine (75 nM) or GCV (5 μM). Cell lysates were harvested at 24 or 72 hpi for Western blotting. B) Cells were seeded at 2 million cells/plate, infected with HCMV Towne and treated with emetine (75 nM) or GCV (5 μM). RNA was harvested and qRT-PCR was performed for p21. Data represent mean±SE of triplicate determinations from a representative of three independent experiments C) HFFs were seeded at 1 or 2 million cells/plate and treated with emetine (75 nM) or GCV (5 μM). Cell lysates were harvested at 72 hpi for Western blotting. D) HFFs were seeded at either 0.5 or 2 million/plate in 100 mm dishes, infected with Towne HCMV followed by treatment with emetine (75 nM) or GCV (5 M) for 24 h. MG132 (10 μM) was added after 12 h. At 24 hpi, lysates were collected and subjected to immunoprecipitation with anti-RPS14 antibody followed by immunoblotting with anti-MDM2 antibody or E) Immunoprecipitation with anti-MDM2 antibody followed by immunoblotting with anti-RPS14 antibody. F) A model showing the mechanism by which emetine disrupts HCMV mediated MDM2-p53 interaction in contact-inhibited cells, but not in cycling cells.
Figure 7B:
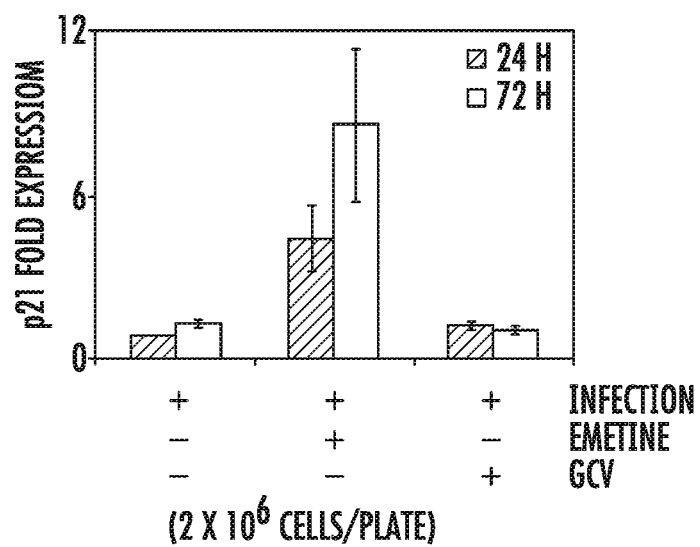
Figure 7C:
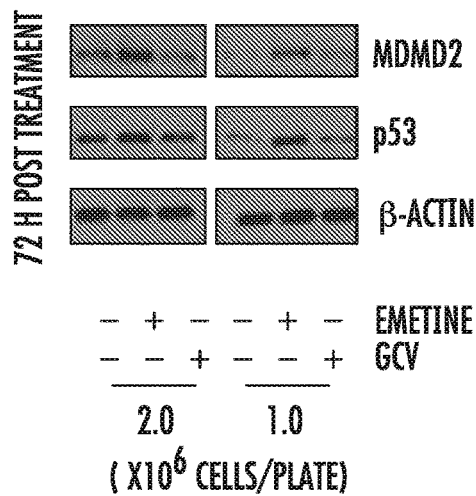

Since emetine inhibited HCMV in contact-inhibited, but not in cycling cells, and induced an interaction between MDM2 and RPS14 in the former, the expression level of cell cycle related proteins, p53 and MDM2, was measured in the contact-inhibited and cycling cells at 24 and 72 hpi. MDM2 expression was reduced after infection and increased with emetine treatment at 72 hpi in contact-inhibited cells (FIG. 7A). The expression of p53 was unchanged with infection and increased with emetine treatment at 72 hpi (FIG. 7A). There was no difference in the expression of either protein among different conditions at 24 hpi or in infected cycling cells at 72 hpi (FIG. 7A). The downstream activity of p53 was measured by qRT-PCR for p21. Emetine treatment resulted in 5.4- and 6.7-fold increase in p21 mRNA at 24 and 72 hpi, respectively in contact-inhibited cells (FIG. 7B, ($p<0.01$). In non-infected cells, the expression level of p53 and MDM2 was increased with emetine treatment, indicating both MDM2 and p53 were stabilized with emetine, irrespective of infection (FIG. 7C).

Figure 7D:
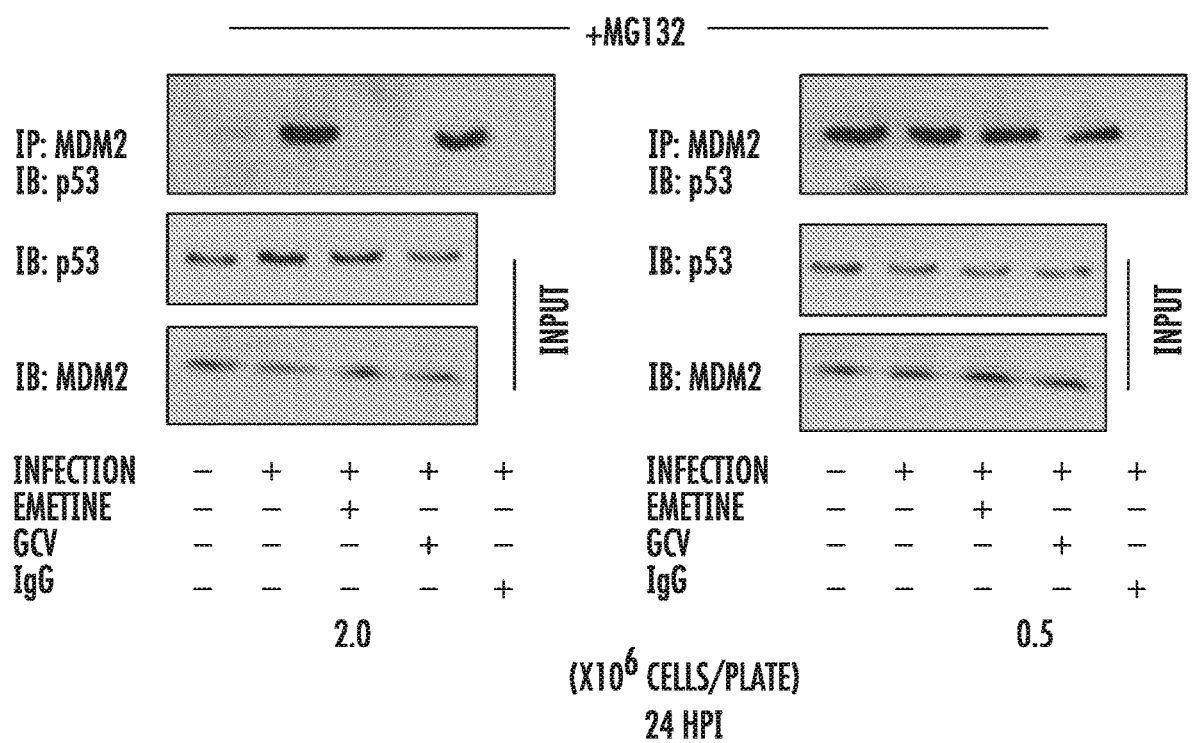
Figure 7E:
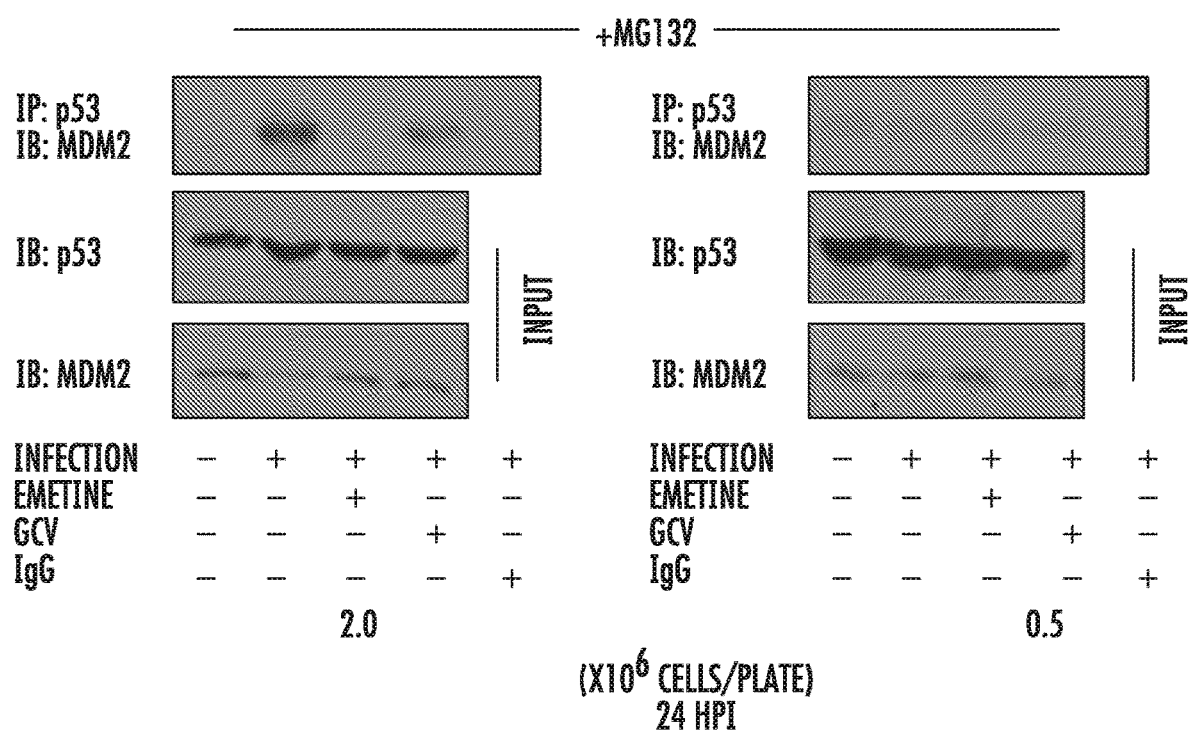
Figure 7F:
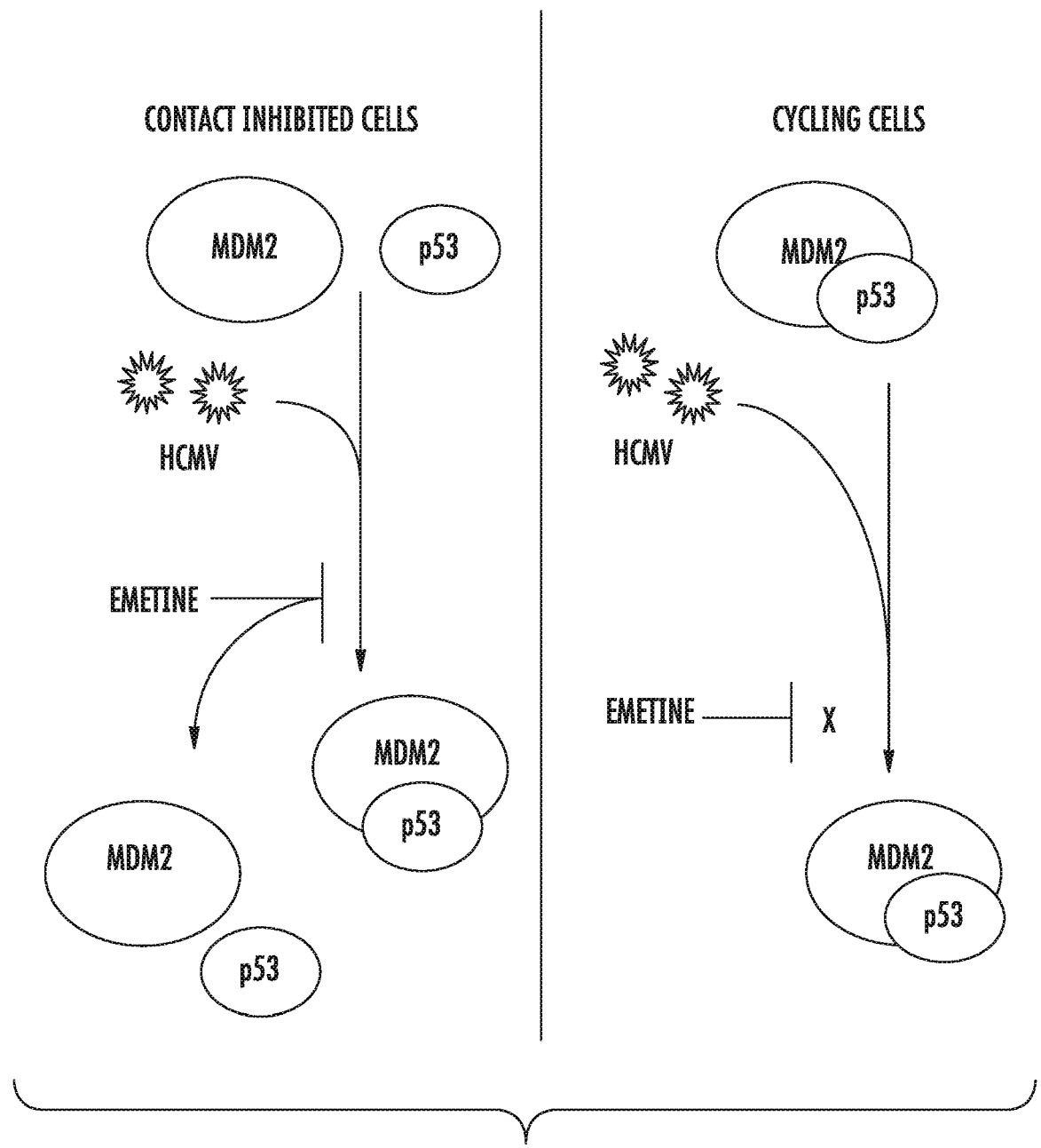

RPS14 has been shown to bind to the acidic domain of MDM2, which is also the binding site for p53. Therefore, the effect of infection and emetine treatment on MDM2-p53 interaction was studied. Since p53 is degraded by the E3 ubiquitin ligase activity of MDM2, MG132 treated samples were used for IP. The interaction between MDM2 and p53 was favored upon infection but disrupted with emetine treatment in contact-inhibited cells, but not in cycling cells (FIG. 7D). A reverse IP confirmed this interaction in infected cells and loss thereof with emetine treatment (FIG. 7E). Our results indicate that emetine disrupts HCMV-induced interaction of MDM2-p53 (model depicted in FIG. 7F). Since the expression of p53 and MDM2 was increased with emetine treatment in non-infected cells, we investigated the status of MDM2-p53-RPS14 interaction in non-infected cells. Although emetine could disrupt MDM2-p53 interaction as observed in HCMV-infected cells, it could not induce MDM2-RPS14 interaction (FIG. 10). Therefore, emetine could perturb the MDM2-p53 interaction irrespective of infection but its ability to associate RPS14 with MDM2 could only be achieved in infected cells.

Finally, the enhanced interaction between RPS14-MDM2 could have effects on HCMV proteins that bind to MDM2. The immediate early 2 (IE2) was reported to interact with MDM2, therefore the effect of emetine on IE2-MDM2 interaction was tested in HEK293 cells. An IP was performed after IE1/2 transfection and emetine treatment. In emetine-treated cells, the interaction of MDM2 and IE2 was significantly decreased, while GCV had no effect on this interaction (data not shown). These results suggest that emetine-induced occupancy of the acidic domain of MDM2 by RPS14 may prevent it from binding IE2.

RPS14 is Indispensable for HCMV Inhibition by Emetine.

Figure 8A:
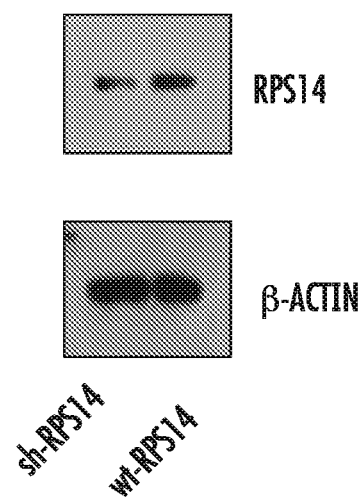
FIGS. 8A-8F: Emetine loses it anti-HCMV activity in RPS14 knockdown cells. A) RPS14 knockdown HFFs were generated from lentiviral system and expression of RPS14 in the knockdown cells was compared to the TRC control cells by Western blotting. B) RPS14 knockdown and control cells were seeded at 2 million/plate in a 96 well plate, infected and treated with emetine (75 nM) or GCV (5 M) for 72 h. Cell viability was determined after 72 h using Cell Titer-Glo assay. C) Luciferase activity was measured in cell lysates. D) Supernatants (30% volume from B) were used to infect HFFs and second cycle luciferase assay was performed. E) Same cell lysates as in B were used to determine HCMV pp65 expression. F) A model showing the mechanism of emetine activity. In contact-inhibited infected cells, emetine displays two functions: (i) it disrupts and stabilizes HCMV-mediated MDM2-p53 interaction; and (ii) it induces translocation of RPS14 into the nucleus. RPS14 likely competes with p53 to interact with free and stable MDM2. The ubiquitin ligase activity of MDM2 may target RPS14 for degradation.
Figure 8B:
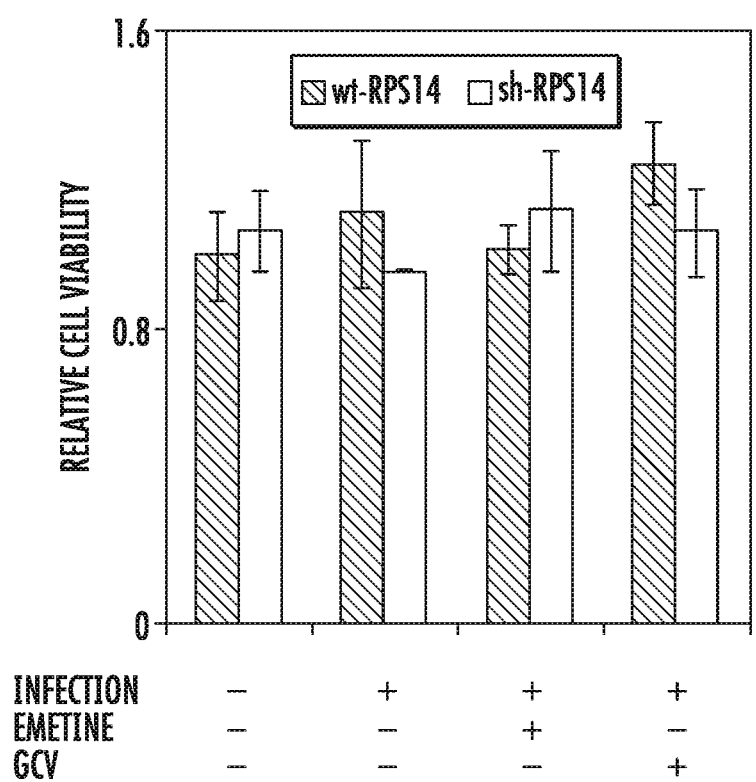
Figure 8C:
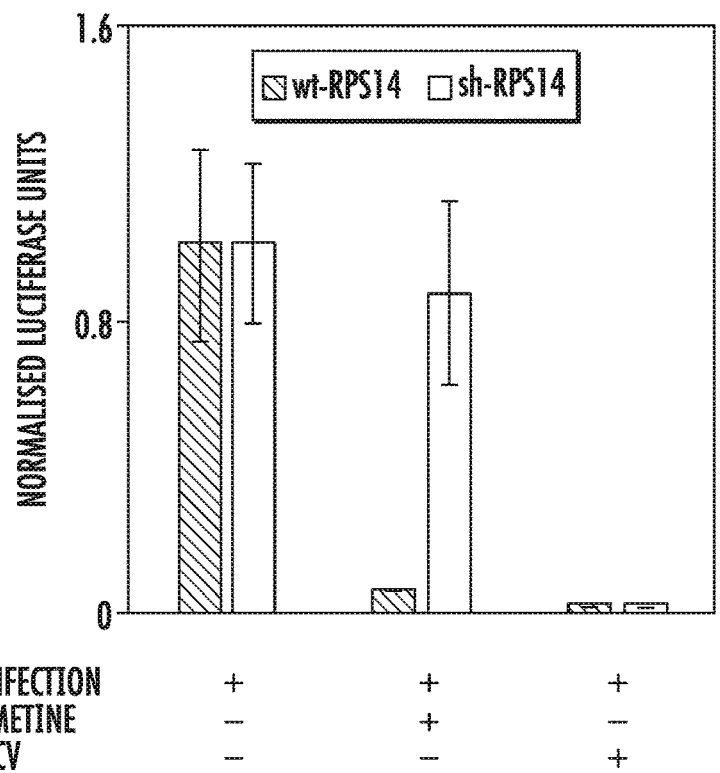

As emetine induced nuclear translocation of RPS14 and its interaction with MDM2, we investigated the anti-HCMV activity of emetine in RPS14 knockdown cells. RPS14 expression was reduced in knockdown cells compared to its expression in control cells (FIG. 8A). Cell viability was similar between wild-type (WT) and RPS14 knockdown cells during infection and drug treatment (FIG. 8B). In contact-inhibited RPS14 knockdown cells, emetine was unable to inhibit HCMV, evident from luciferase assay after first and second cycle, (FIGS. 8 C, D) and pp65 expression at 72 hpi (FIG. 8E), indicating the requirement of RPS14 for emetine activities.

Discussion

The existing antiviral drugs effectively suppress HCMV replication, but their considerable side effects, and selection of resistant viral strains, call for the identification of new HCMV inhibitors. HCMV perturbs a myriad of cellular signaling pathways for its own benefit of replication and survival, some of which could serve as novel targets for virus inhibition. We report here on the anti-HCMV activities of emetine at low nM concentration (FIG. 1), and its mode of action through targeting the interaction of RPS14-p53-MDM2, thus providing a novel host-dependent antiviral approach. Emetine inhibited GCV-resistant HCMV and HSV1&2 at nM concentrations as well (FIG. 1C). Inhibition of HCMV replication by emetine occurred after virus entry and before the activities of GCV (FIG. 2). MCMV was inhibited at low 0.1 mg/kg based on plaque assay from salivary gland and liver and quantitative PCR from blood. There was no significant difference in MCMV inhibition between 0.1 and 1 mg/kg. Plaque number was lower in liver compared to the salivary gland (as expected), but virus was inhibited in both organs (FIG. 3).

Figure 8D:
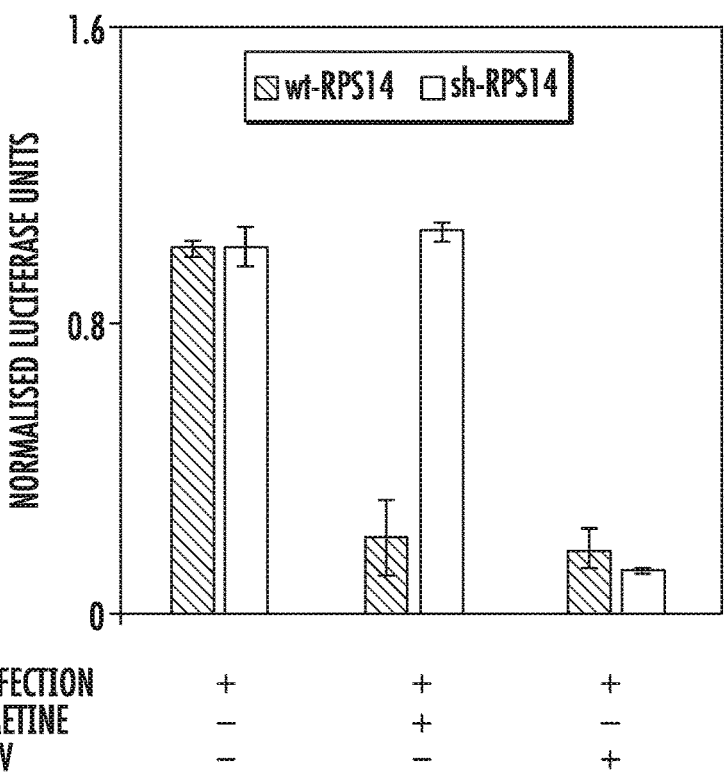
Figure 8E:
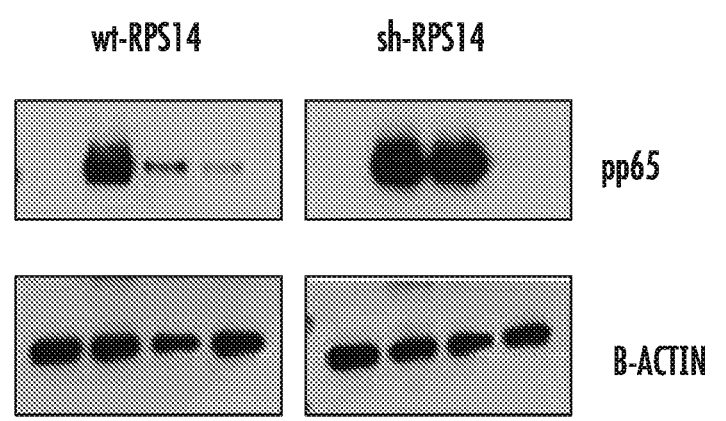
Figure 8F:
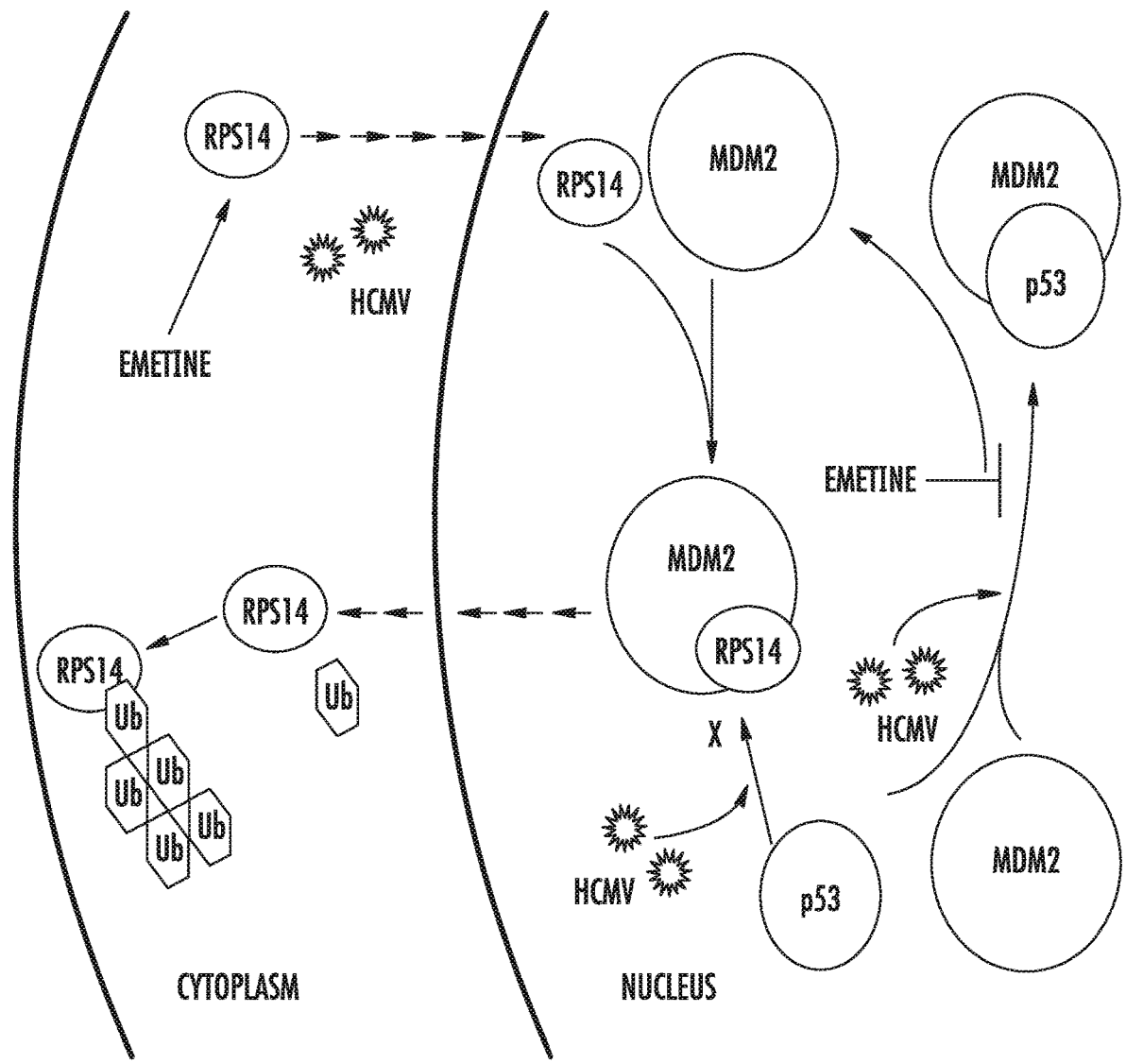

The observed decrease in emetine activity against HCMV in cycling cells as compared to contact-inhibited cells (FIG. 4), and a previous study that correlated emetine resistance in Chinese hamster ovary cells with mutations in RPS14, prompted us to investigate the role of RPS14 in HCMV replication (summarized in a model, FIG. 8D). HCMV induces multiple ribosomal proteins, but the requirement of specific ribosomal proteins for its replication has not been studied. Our results show that HCMV induces RPS14 during infection, likely as strategy for viral protein synthesis (FIG. 5). In cycling non-infected cells, higher expression of RPS14 were observed compared to contact-inhibited cells, suggesting cycling cells are more active in synthesizing proteins for ongoing growth and division. Our results show that reduced RPS14 expression with emetine treatment at 72 hpi is a result of its degradation, which is consequential to its interaction with MDM2. The reported interaction of RPS14 with MDM2 directed us to investigate the role of RPS14 in the setting of MDM2-p53 interaction in HCMV replication (summarized in a model, FIG. 8D). Emetine treatment resulted in improved interaction between RPS14 and MDM2 in infected contact-inhibited cells. In uninfected cells (FIG. 5C, D) the interaction was not modified by emetine, likely because it did not translocate RPS14 into the nucleus (FIG. 10). In infected cells emetine induced RPS14 translocation into the nucleus (FIG. 6A), where it could interact with MDM2 and compete with other viral proteins, such as IE2 (FIG. 11) and cellular proteins such as p53 on the acidic domain of MDM2 (FIG. 7C, D). Although the binding site of MDM2-IE2 has not been characterized, it is possible that through RPS14 binding to MDM2, IE2 is incapable of binding to MDM2. Later during infection RPS14 relocalized to the cytoplasm, was ubiquitinated and degraded (FIG. 6B). RPS14 interacted with MDM2 at 24 hpi (FIG. 5C), but its expression level was similar at all tested conditions (FIG. 4A), suggesting that at this time point a balance between virus-induced RPS14 and its emetine-triggered degradation was still maintained. However, at 72 hpi, when virus replication was sufficiently inhibited, a significant reduction in the expression of RPS14 was observed in emetine treated condition, indicating emetine-mediated RPS14 degradation (FIG. 5A).

The dependence of emetine activity against HCMV on cell density at the time of infection (FIG. 4) suggested that RPS14 interaction with the cell cycle regulators MDM2 and p53 may contribute to its activities. Reduced expression level of MDM2 during HCMV infection has been reported (16), and also shown here at 72 hpi (FIG. 6A). Although infection induces p53 expression and results in reduced p53 activity, at MOI 1 we did not observe changes in p53 expression. Emetine treatment resulted in increased p53 activity in infected cells, evidenced by p21 mRNA expression (FIG. 7B). Levels of MDM2 and p53 were stabilized with emetine (FIG. 7A, C), suggesting their interaction might be modified by the drug. Our data reveal that while MDM2-p53 interaction is required for HCMV replication, emetine disrupts this interaction by 24 h, resulting in stabilization of each interacting partner (FIG. 7D). In infected cycling cells in which HCMV escaped from emetine suppression (FIG. 4), MDM2-p53 interaction was not disrupted by the drug (FIG. 7D, E). Notably, in cycling non-infected cells the interaction between MDM2 and p53 was more significant than in the contact-inhibited cells, suggesting it prevents p53-mediated cell cycle arrest (FIG. 7D, E). However, in contact-inhibited cells, disruption of MDM2-p53 interaction takes place and in cycling cells, the p53 protein is targeted for degradation by interaction with MDM2.

The p53 protein binds to MDM2 at the acidic domain (amino acid residues 235-300). RPS14 also binds to the same acidic domain of MDM2 at a significantly overlapping region with the p53 binding site (amino acid residues 215-300). Therefore, RPS14 may be competing with p53 for the same binding domain on MDM2. The reported mutations in the C-terminus domain of RPS14 that lead to emetine resistance; Arg-149-Cys and Arg-150-His, may imply altered binding to MDM2. With a higher number of amino group and proton donor, Arg may have higher affinity for the acidic domain of MDM2 as compared to His or Cys. Alternatively, haploinsufficiency of RPS14 may play a role in the interaction of MDM2-p53. These hypotheses will be tested in future studies.

In HCMV-infected cells binding of RPS14 to MDM2 was required for emetine activities. In cycling cells, MDM2 and p53 already interacted, resulting in even higher affinity of MDM2 for p53, and the acidic domain of MDM2 was already occupied by p53. Therefore, RPS14 could not bind to MDM2 resulting in loss of emetine activity against HCMV. In contrast, in contact-inhibited cells, emetine induced RPS14 binding to the free MDM2-acidic domain and prevented virus-mediated interaction between p53 and MDM2, resulting in stabilization of p53 and MDM2. These findings were also supported by the early activity of emetine (FIG. 2B). If added after 12 hpi, emetine failed to inhibit virus, since by that time HCMV may engage most of the p53 with MDM2 resulting in blocking of the RPS14 binding site on MDM2. Although in non-infected cells, emetine stabilized MDM2 and p53 in both cycling and contact-inhibited cells (FIG. 7C), it could not induce the nuclear translocation of RPS14 or its binding with MDM2 (FIG. 10). Future studies will address the consequences of disruption of MDM2-p53 binding and stabilization of p53 and MDM2 as a cellular strategy for HCMV inhibition.

Our results show efficient inhibition of HCMV replication in vitro and MCMV replication in vivo, suggesting that repurposing of emetine at a much lower dose may provide therapeutic/prophylactic strategy for HCMV through host-directed antiviral mechanism. Although the route of administration and potential cumulative toxicities must be considered, the doses required for virus inhibition are significantly lower than the traditional doses used in clinical practice. For amebiasis, emetine has been administered intramuscularly or subcutaneously daily at 1 mg/kg (maximal dose of 60 mg) for up to 10 days. Severe side effects occurred rarely and were only observed at high doses. Emetine was well-tolerated when delivered intravenously at 1.5 mg/kg doses twice a week in clinical trials as an anti-tumor agent. Patients treated with 1 mg/kg emetine daily via subcutaneous injection for 10 days did not experience any notable toxicity. Extrapolating from a total of 600 mg amoebiasis dosing to HCMV dosing, 1000 times more drug would need to be administered to reach the same cumulative dose. The therapeutic plasma concentration of emetine is 0.005-0.075 μg/mL, and its half-life→24-48 h. As described herein, the in vitro data suggest that at therapeutic plasma concentration HCMV replication can be fully inhibited. In addition, the PK studies support wide and prolonged tissue distribution, which may be an important factor for HCMV inhibition. The present invention provides evidence for the first time for use of an old agent with distinct cellular activities resulting in HCMV inhibition.

Example 2: Prospective Pharmacokinetic Study of Low Dose Emetine in Healthy Volunteers CMV is an important pathogen, causing severe morbidity and mortality in transplant recipients and congenitally-infected children. GCV and other DNA polymerase inhibitors are used in patients with CMV disease, but all cause intolerable toxicities and drug-resistant viruses emerge during therapy. There is an absolute need for novel treatment strategies for CMV. Emetine exhibits efficient inhibition of CMV replication in vitro and in a mouse model in vivo, suggesting that its repurposing at a much lower dose may provide therapeutic strategy for CMV through host-directed anti-viral mechanism. The doses required for virus inhibition are significantly lower than the traditional doses used in clinical practice. Low dose emetine can also provide a new therapeutic strategy for Herpesvirus 1 and 2.

Established clinical experience with emetine provides the basis for typical safe dosage, maximum tolerated dose, and acute and chronic toxicity of emetine in humans. There are some historical plasma PK data of emetine. Primary safety concern of emetine is cardiotoxicity, which derives from cumulative dose rather than maximum concentration.

Early clinical investigations reported ECG changes after SC treatment of amebaisis with emetine (Dack, S. & Moloshok, R. Cardiac manifestations of emetine toxicity in amebic dysentery. Proc Am Fed Clin Res 3, 101 (1947); Dack, S. & Moloshok, R. E. Cardiac manifestations of toxic action of emetine hydrochloride in amebic dysentery. Arch Intern Med (Chic) 79, 228-238 (1947); and Klatskin, G. & Friedman, H. Emetine toxicity in man; studies on the nature of early toxic manifestations, their relation to the dose level, and their significance in determining safe dosage. Ann Intern Med 28, 892-915 (1948)). The total dose of emetine was as high as 1.42-1.75 gm, but no permanent cardiovascular changes were observed. The onset of ECG changes was variable and in some cases did not appear until after the treatment was stopped. In a study of 30 patients treated with 60 mg/day emetine hydrochloride IM for six days and three days with a three-day rest in between, no cardiac insufficiency or arrhythmias developed (Banerjea, J. C. The effect of emetine therapy on the cardiovascular system. J Assoc Physicians India 14, 349-364 (1966)). ECG changes occurred in 63% of patients (T-wave inversion and prolongation of the Q-T interval). No serious cardiotoxicity was observed. A similar conclusion was drawn by another study in 54 patients (Ramachandran, S. Adverse effects of emetine therapy. Ceylon Med J 18, 138-143 (1973)). The effect of emetine on serum transaminases was investigated in 30 patients treated with 60 mg/day emetine IM for 6-9 days (Kini, P. M., Venugopal, N. S., Santhamma, K. M. & Rao, R. R. The effect of emetine on the electrocardiogram and the serum transaminases. J Assoc Physicians India 17, 457-461 (1969)). ECG changes were observed in 40% of patients, with T-wave changes being the most common. Rise in SGOT enzyme was associated with the development of ECG changes, but clear correlation could not be determined. SGOT decreased abruptly after drug discontinuation. SGPT, bilirubin, and alkaline phosphatase were unchanged, thus it was suggested that elevated SGOT could indicate heart or skeletal muscle damage. CPK elevation has been reported during and after emetine treatment (Siddiqui, S., Firat, D. & Olshin, S. Phase II study of emetine (NSC-33669) in the treatment of solid tumors Cancer Chemother Rep 57, 423-428 (1973); Kane, R. C., et al. Phase I-II evaluation of emetine (NSC-33669) in the treatment of epidermoid bronchogenic carcinoma. Cancer Chemother Rep 59, 1171-1172 (1975)), but did not correlate with ECG changes.

For amebiasis therapy, dehydroemetine was claimed to be superior to emetine because of its similar amebicidal activities and less toxicity (Rollo, I. M. Antiplasmodial efficacy of 2,4-diaminopyrimidine sylfonamide combinations, especially against chloroquine-resistant malaria. Can Med Assoc J 112, 50-53 (1975)). Similar ECG changes have been reported, but at similar doses, their incidence was lower for dehydroemetine (Powell, S. J., Wilmot, A. J., Macleod, I. N. & Elsdon-Dew, R. A comparative trial of dehydroemetine, emetine hydrochloride and chloroquine in the treatment of amoebic liver abscess. Ann Trop Med Parasitol 59, 496-499 (1965); Powell, S. J., Wilmot, A. J., Macleod, I. N. & Elsdon-Dew, R. A comparative trial of dehydroemetine and emetine hydrochloride in identical dosage in amoebic liver abscess. Ann Trop Med Parasitol 61, 26-28 (1967)). Although the action of emetine is cumulative, many of the toxic manifestations were transient and subsided in spite of further drug administration. Some of these were; diarrhea, nausea, EKG changes. The latter were transient, indicating that the myocardial effects of emetine at therapeutic doses for amebiasis are reversible. Emetine-induced neuritis has been reported at doses exceeding 1 gram. Although most studies used emetine SC, large doses were well-tolerated when emetine was sealed in a material designed to withstand digestion for 3-4 h (Shrapnel, B. C., Johnson, C. M. & Sandground, J. H. Oral emetine in the treatment of intestinal amebiasis Am J Trop Med Hyg 26, 293-310 (1946)). Lastly, successful treatment of malaria was reported in 17 patients treated with 40 mg IM×6 daily doses with no reported toxic effects (James, R. F. Malaria treated with emetine or metronidazole. Lancet 2, 498 (1985)).

Hypothesis:

In healthy research participants, a low subcutaneous dose of emetine is well-tolerated and achieves the target concentration within 2-fold or above the anti-CMV concentration identified in BALB/c mouse experiments (described above).

Objectives:

To determine the safety, pharmacokinetic (PK) and bio-distribution of emetine at each of 2 dose levels in healthy research participants.

Endpoints:

(1) Adverse event grading according to the Division of AIDS (DAIDS) toxicity tables; (2) Compartmental and non-compartmental plasma PK parameters for each of two cohorts, including assessment of dose-proportionality between cohorts.

Study Population:

Healthy men and women >18 yr of age will be eligible for the PK study.

Study Design:

This will be a Phase 0, two dose level open label study to determine the safety and non-compartmental PK of emetine.

Dosage and Administration:

The final clinical dose target is chosen to be the equivalent of the 0.1 mg/kg BALB/c mouse dose in the CMV experiments described above. For a margin of safety, the study begins at ⅓ of this dose. Concentration estimates at peak and for several days during elimination phase are estimated based on prior clinical PK data from ipecac which shows a 2-compartment model with significant distribution phase and long half-life of ~24-48 hours. Based on the more conservative 24-hour half-life and an established emetine assay lower limit of quantitation of 0.1 ng/mL, it is anticipated being able to measure emetine for 3 days after dosing at the target dose which provides 3 half-lives with which to make reasonable half-life estimates. If the half-life is longer, it will be possible to measure emetine proportionally longer. Estimates are based on PK parameter assumptions described in the footnote of Table 1. Peak concentrations (Cmax) estimates are calculated based on both mouse data (dose-proportional using allometric scaling) and prior clinical data (dose-proportional using syrup of ipecac studies).

TABLE 1

Dosing Estimates of SC Emetine in Humans

| Target Ratio | Mouse oral dose mg/kg | Human Oral Dose[1] mg/kg | Human SC dose[1] mg/kg | Ipecac ratio[2] | Cmax Mouse[3] ng/mL | Cmax Ipecac[4] ng/mL | C48h[5] ng/mL | C72h[5] ng/mL |
|---|---|---|---|---|---|---|---|---|
| 1/3X | 0.033 | 0.0027 | 0.0031 | 0.06 | 0.5 | 1.0 | 0.12 | 0.06 |
| 1X | 0.100 | 0.0080 | 0.0094 | 0.17 | 1.4 | 3.1 | 0.35 | 0.18 |

[1]Assumptions: $F_{PO}$ = 0.31, $F_{SC}$ = 0.85, half-life 24 h.
[2]Ipecac ratio based on planned human SC doses relative to oral Ipecac 11 mg dose.
[3]$C_{max}$ based on BALB/c experiments reported above where 0.1 mg/kg achieved $C_{max}$ 1.4 ng/mL.
[4]$C_{max}$ Ipecac is based on Ipecac ratio times observed clinical $C_{max}$.
[5]$C_{48h}$ and $C_{72h}$ based on 24 hour half-life. Longer half-life will result in higher estimated concentrations.

The dose is prepared by the Johns Hopkins Hospital Investigational Drug Service (IDS) Pharmacy according to US historical use as described in the USP monograph. Emetine API is provided by the NCATS collaborators according to GMP standards and delivered to the Hopkins IDS. On the day of dosing, the IDS prepares a unit dose for SC injection by dissolution of the API in sterile water based on each individual participant's body weight to achieve a final dose of 0.003 mg/kg (Cohort 1) or 0.009 mg/kg (Cohort 2).

Dose Escalation/Adjustment Criteria:

Three participants are evaluated in cohort 1. If no participants experience grade 3 toxicity, then the study escalates to cohort 2 in which 6 research participants are evaluated. If 1 of 3 research participants experiences grade 3 or more toxicity in Cohort 1, then an additional 3 research participants are enrolled at that dose level. If a second participant experiences grade 3 or 4 toxicity, then the study is stopped. There are no reductions in dose as the mouse activity occurred at concentrations higher than those anticipated in cohort 1. Similarly, if any 2 research participants experience grade 3 or higher toxicity in Cohort 2, then the enrollment is stopped. Interim analysis of data for Cmax and AUC is completed following the first 3 research participants at each cohort level. If the median Cmax for Cohort 1 does not meet or exceed the mouse Cmax value in Table 1, then the dose for Cohort 2 is adjusted upwards proportionally to achieve the Cmax achieved at the 0.1 mg/kg level in the mouse studies (the level associated with anti-CMV activity).

Study Procedures

Screening: Screening to determine study eligibility is established based on medical history, physical examination, ECG, and routine laboratory evaluation (chemistry, hematology). Pregnant women, research participants with a known sensitivity to emetine or those who have received any investigational drug, during the 30 days prior to enrollment are excluded. Screening evaluations will be valid for 28 days.

TABLE 2

Schedule of Events.

| Phase | Screen | Inpatient | | | Outpatient | | | |
|---|---|---|---|---|---|---|---|---|
| Study Day Administrative/ Ethics | <-28 | 0 | 0 | | 1 | 2 | 3 | 5 |
| ICF, Eligibility Clinical/Safety | X | | | | | | | |
| History/ Physical/AEs | X | X | | | X | X | X | X |
| Hematology, Chemistry | X | X | | | X | | X | X |
| ECG | | X | | | X | | X | X |
| Study Product | | | | | | | | |
| SC injection | | 0 hours | | | | | | |
| Study readouts | | | | | | | | |
| Plasma | | Pre-dose | 0.25, 0.5, 1, 1.5, 2, 3, 4, 6, 8, 12 | 24, 32 | 48 | 72 | 96 | |

Plasma samples are taken within 30 minutes before dosing and at indicated hours after SC dose.

Dosing and Sample Collection:

Eligible research participants arrive at the study site in the morning around 7:30 AM and undergo interim history and directed physical examination. Screening laboratory studies (chemistry, hematology) are repeated and used for baseline values, but not to further exclude research participants. Emetine is administered by SC injection based on cohort dose, either 0.003 mg/mg (Cohort 1) or 0.009 mg/kg (Cohort 2). Blood samples are obtained pre-dose, at 0.25, 0.5, 1, 1.5, 2, 4, 6, 8, 12, 24, 32, 48, 72, and 96 hours post-dose. For both safety and logistical reasons, research participants remain in the research clinic for 24 hours after completion the dose. Research participants have safety evaluation each morning associated with a clinic visit (24, 48, 72, 96 hours) to include interim history and targeted physical examination. ECG and laboratory evaluation (chemistry, hematology) also occurs at 24, 72, and 96 hours post dose. Any abnormalities identified by history, physical examination, or laboratory test, are followed until resolution. All adverse events encountered during the clinical study are reported on the Case Report Form (CRF) that is prepared for this study.

Safety is monitored by recording and assessing adverse events and abnormal laboratory values. To maximize safety, cardiovascular function is monitored. Any abnormalities identified by history, physical examination, or laboratory test, are followed until resolution. All adverse events encountered during the clinical study are reported on the Case Report Form (CRF) that is prepared for this study. A trained regulatory manager assists the group in IRB and FDA reporting.

Data analysis: Adverse events, grade, and attribution to study drug are tabulated and summarized using descriptive statistics. PK parameters are estimated using standard intensive PK methods for non-compartmental and compartmental data analysis. Non-compartmental estimates for each research participant are calculated and include area under the curve (AUC), maximum serum concentration (Cmax), time to Cmax (Tmax), terminal elimination half-life (t1/2), clearance (Cl/F), and volume of distribution (Vd/F). Compartmental PK parameters include (insofar as the data allow), Cmax, AUC0-inf, % AUCextrapolated, Cl/F, V/F, intercompartmental clearance (Q), elimination rate constant (ke), absorption rate constant (ka), distribution rate constant (kd), PK parameter estimates are summarized using descriptive statistics, including, means, standard deviations, medians, and ranges. Cmax and AUC are assessed for dose proportionality using dose-adjusted median values by cohort. Resultant PK parameters aid in determining the appropriate multi-dose regimen to achieve target serum concentration via PK model simulations.

With the progress in transplantations, and the increasing number of people living with organ or bone marrow transplant, treatment for CMV becomes a major challenge. Not infrequently CMV infection affects graft survival, morbidity and mortality. The FDA-approved antiviral agents suppress CMV replication, but prolonged courses of therapy lead to emergence of drug resistant mutants. A recent retrospective review from Johns Hopkins highlights the toxicities associated with foscarnet (Avery, R. K., et al. Outcomes in Transplant Recipients Treated with Foscarnet for Ganciclovir-Resistant or Refractory Cytomegalovirus Infection. Transplantation (2016)). Through NIH-funded project for high throughput screening, the present inventors identified emetine as a CMV inhibitor at low nM doses.

Because the rate of excretion of emetine is slow, the ingestion of daily oral doses may produce an accumulation that approaches the fatal parenteral dose, which has been estimated to be 600-1250 mg in adults (Palmer, E. P. & Guay, A. T. Reversible myopathy secondary to abuse of ipecac in patients with major eating disorders. N. Engl. J. Med 313, 1457-1459 (1985)). In a 70 kg person one month of emetine dosing for CMV at 0.008 mg/kg (extrapolated dose from the mice data to human dosing) will result in a cumulative dose of 7 mg (10 doses total), or 21 mg (30 doses total). Studies of amebiasis have shown ECG abnormalities when the total doses of emetine were 1.75 gm. No permanent cardiovascular changes were observed. The reported ECG changes can be monitored during therapy, and may not be significant at the low dose. Although the accumulated clinical experience indicates that patients treated with emetine do not have long-lasting myocardial damage, the observed inhibition of protein synthesis in vitro by emetine led to investigation of this question. There was no effect of emetine on cardiac protein synthesis (Yang, W. C. & Dubick, M. Mechanism of emetine cardiotoxicity. Pharmacol. Ther 10, 15-26 (1980)). Thus, the in vitro studies of protein inhibition may not apply to in vivo after chronic emetine treatment. We have reported that at concentration that inhibit CMV replication in vitro there was no inhibition of protein synthesis by emetine (Mukhopadhyay, R., et al. Efficacy and Mechanism of Action of Low Dose Emetine against Human Cytomegalovirus. PLoS Pathog 12, e1005717 (2016)). In fact, at the nM dosing and based on the present inventors' investigation of the mechanism of action of emetine, the expression level of some cellular proteins (such as MDM2 and p53) was increased. Taken together, the present inventors propose a new strategy for CMV therapeutics, based on repurposing of an old agent that was used in the past at much higher doses.

---

We claim:

1. A synergistic pharmaceutical composition comprising (a) emetine; (b) ganciclovir; and (c) a pharmaceutically acceptable carrier.

2. The pharmaceutical composition of claim 1, wherein the pharmaceutical composition further comprises an adjuvant.

3. A method for treating HCMV in a patient in need thereof comprising administering to the patient the synergistic pharmaceutical composition of claim 1.

4. A method for treating HCMV in a patient in need thereof comprising administering to the patient a therapeutically effective amount of emetine in combination with ganciclovir, wherein the combination has synergistic effect in treating HCMV.

* * * * *